United States Patent
Bishay et al.

(10) Patent No.: US 6,622,051 B1
(45) Date of Patent: Sep. 16, 2003

(54) PERCUTANEOUS ELECTRICAL THERAPY SYSTEM WITH ELECTRODE ENTRY ANGLE CONTROL

(75) Inventors: Jon M. Bishay, Woodinville, WA (US); Paul Leonard, Woodinville, WA (US)

(73) Assignee: Vertis Neuroscience, Inc., Seattle, WA (US)

( * ) Notice: Subject to any disclaimer, the term of this patent is extended or adjusted under 35 U.S.C. 154(b) by 0 days.

(21) Appl. No.: 09/452,477

(22) Filed: Dec. 1, 1999

(51) Int. Cl.⁷ .............................. A61N 1/00; A61N 1/05
(52) U.S. Cl. ............................ 607/116; 607/2; 606/129
(58) Field of Search ................................. 607/116, 1, 2, 607/46; 600/372, 373, 377; 606/129, 108

(56) References Cited

U.S. PATENT DOCUMENTS

| | | |
|---|---|---|
| 3,030,959 A | 4/1962 | Grunert |
| 3,090,151 A | 5/1963 | Stewart et al. |
| 3,208,452 A | 9/1965 | Stern |
| 3,938,526 A | 2/1976 | Anderson et al. |
| 3,943,935 A | 3/1976 | Cameron |

(List continued on next page.)

FOREIGN PATENT DOCUMENTS

FR    2 500 745    9/1982

OTHER PUBLICATIONS

AAMI Neurosurgery Committee; AAMI Implantable Neurostimulator Subcommittee. Implantable peripheral nerve stimulators. Assoc. for the Advancement of Medical Instrumentation (1995) NS15–1995. cover–8, 11 pages.**

(List continued on next page.)

*Primary Examiner*—George R. Evanisko
(74) *Attorney, Agent, or Firm*—Perkins Coie LLP

(57) ABSTRACT

A percutaneous electrical therapy system with electrode angle of entry control, wherein the system includes a control unit; an electrode electrically connectable to the control unit to deliver electrical therapy to a patient, the electrode having a sharp point at a distal end adapted to be inserted into a patient's tissue; and an electrode angle of insertion assembly controlling the electrode's angle of entry into the patient's tissue. The invention also includes the percutaneous electrode and electrode angle of insertion assembly described above apart from the control unit.

The invention is also a method of performing percutaneous electrical therapy including the steps of: aligning an electrode assembly housing with a patient's tissue; inserting a sharp point of an electrode into the patient's tissue, the housing supporting the electrode during insertion to control the electrode's angle of insertion; and applying an electrical signal to the electrode from a control unit.

13 Claims, 15 Drawing Sheets

U.S. PATENT DOCUMENTS

| | | | |
|---|---|---|---|
| 3,983,881 A | 10/1976 | Wickham | |
| 4,139,011 A | 2/1979 | Benoit et al. | |
| 4,207,903 A | 6/1980 | O'Neill | |
| 4,256,116 A | 3/1981 | Meretsky et al. | |
| 4,262,672 A | 4/1981 | Kief | |
| 4,281,659 A | 8/1981 | Farrar et al. | |
| 4,408,617 A | 10/1983 | Auguste | |
| 4,431,000 A | 2/1984 | Butler et al. | |
| 4,512,351 A | 4/1985 | Pohndorf | |
| 4,541,432 A | 9/1985 | Molina-Negro et al. | |
| 4,556,064 A | 12/1985 | Pomeranz et al. | |
| 4,685,466 A | 8/1987 | Rau | |
| 4,712,558 A | 12/1987 | Kidd et al. | |
| D297,047 S | 8/1988 | Hon et al. | |
| 4,895,154 A | 1/1990 | Bartelt et al. | |
| 4,934,371 A | 6/1990 | Malis et al. | |
| 4,953,564 A | 9/1990 | Berthelsen | |
| 5,012,811 A | 5/1991 | Malis et al. | |
| D318,330 S | 7/1991 | Doty et al. | |
| 5,036,850 A | 8/1991 | Owens | |
| 5,054,486 A | 10/1991 | Yamada | |
| 5,094,242 A | 3/1992 | Gleason et al. | |
| 5,117,826 A | 6/1992 | Bartelt et al. | |
| 5,211,175 A | 5/1993 | Gleason et al. | |
| 5,246,014 A | 9/1993 | Williams et al. | |
| 5,255,691 A | 10/1993 | Otten | |
| 5,281,218 A | 1/1994 | Imran | |
| 5,332,401 A | 7/1994 | Davey et al. | |
| D357,069 S | 4/1995 | Plahn et al. | |
| 5,417,719 A | 5/1995 | Hull et al. | |
| 5,423,314 A | 6/1995 | Schmid | |
| 5,439,440 A | 8/1995 | Hofmann | |
| 5,449,378 A | 9/1995 | Schouenborg | |
| 5,593,429 A | 1/1997 | Ruff | |
| 5,649,936 A | * 7/1997 | Real ........................... | 606/130 |
| 5,682,233 A | 10/1997 | Brinda | |
| 5,702,359 A | 12/1997 | Hofmann et al. | |
| 5,810,762 A | 9/1998 | Hofmann | |
| 5,861,015 A | 1/1999 | Benja-Athon | |
| 5,873,849 A | 2/1999 | Bernard | |
| 5,928,144 A | 7/1999 | Real | |
| 5,941,845 A | 8/1999 | Tu et al. | |
| 5,948,008 A | 9/1999 | Daikusono | |
| 5,968,063 A | 10/1999 | Chu et al. | |
| 6,009,347 A | * 12/1999 | Hofmann ..................... | 604/21 |
| 6,035,236 A | 3/2000 | Jarding et al. | |
| 6,050,992 A | 4/2000 | Nichols | |
| 6,068,650 A | 5/2000 | Hofmann et al. | |
| 6,122,547 A | 9/2000 | Benja-Athon | |
| 6,208,893 B1 | 3/2001 | Hofmann | |
| 6,304,785 B1 | 10/2001 | McCreery et al. | |

OTHER PUBLICATIONS

Almay, B.G.L. et al., "Long–Term High Frequency Transcutaneous Electrical Nerve Stimulation (hi–TNS) in Chronic Pain. Clinical Response and Effects of CSF–Endorphins, Monoamine Metabolites. Substance P–Like Immunoreactivity (SPLI) and Pain Measures", J. Physchosom.Res. (1985) 29:247–257, 11 pages.

Baker, L. et al., "Effects of Waveform on Comfort During Neuromuscular Electrical Stimulation", Clinical Orthopedics and Related Research (Aug. 1988) 233:75–85.

Brull, S., Silverman, D.G., "Pulse Width, Stimulus Intensity, Electrode Placement, and Polarity During Assessment of Neuromuscular Block", Anesthesiology (Oct. 1995) 83:702–709.

Carroll, D., "Randomization is Important in Studies with Pain Outcomes: Systematic Review of Transcutaneous Electrical Nerve Stimulation in Acute Postoperative Pain", Br J Anaesth. (1996) 77:798–803**.

Cassutto, J. et al., "The Use of Modulated Energy Carried on a High Frequency Wave for the Relief of Intractable Pain", Int.J.Clin.Pharm.Res. (1993) XIII(4) 239–241**.

Eclipsc+ Dual Channel Transcutaneous Electrical Nerve Stimulator User's Manual (1993), 31 pages**.

Electrotherapy for Rehabilitation, Empi Cervical Traction, http://www.empi.com/b/b2–htm. Oct. 22, 2001, 3 pages.

EPIX XL TENS Instruction Manual, Empi, Inc. (1988), 21 pages**.

Foster, N. et al., Manipulation of Transcutaneous Electrical Nerve Stimulation Variables Has No Effect on Two Models of Experimental Pain in Humans, The Clinical Journal of Pain (1996) 12:301–310**.

Gopalkrishnann, P., Sluka, K.A., "Effect of Varying Frequency, Intensity, and Pulse Duration of Transcutaneous Electrical Nerve Stimulation on Primary Hyperalgesia in Inflamed Rats", Arch.,Phys.Med. Rehabil. (Jul. 2000) 81:984–990.

Gracanin, F., Trnkoczy, A. "Optimal Stimulus Parameters for Minimum Pain in the Chronic Stimulation of Innervated Muscle", Arch.Phys.Med. Rehabil. (Jun. 1975) 56:243–249.

Hamza, M.A. et al., "Effect of the Duration of Electrical Stimulation on the Analgesic Response in Patients with Low Back Pain", Anesthesiology (Dec. 1999). V. 91, No. 6:1622–7.

Hamza MA et al., "Effect of the frequency of transcutaneous electrical nerve stimulation on the postoperative opioid analgesic requirement and recovery profile", Anesthesiology (Nov. 1999) 91:1232–8.

Hans JS et al., "Effect of Low and High–Frequency TENS on Met–enkephalin–Arg–Phe and Dynorphin A Immunoreactivity in Human Lumbar CSF", Pain (1991) 47:295–8**.

Instruction Manual for the Empi EPIX VT TENS Device, 1997, Dual Channel Transcutaneous Electrical Nerve Stimulator, Empi, Inc., 29 pages.**

Jette, D., "Effect of Different Forms of Transcutaneous Electrical Nerve Stimulation on Experimental Pain", Physical Therapy (Feb. 1986) 66:2, 187–193.

Johnson, M.I., "Analgesic Effects of Different Pulse Patterns of Transcutaneous Electrical Nerve Stimulation on Cold–induced Pain in Normal Subjects", Journal of Psychosomatic Research (1991) 35:2–3; 313–321**.

Johnson, MI, "Analgesic Effects of Different Frequencies of Tanscutaneous Electrical Nerve Stimulation on Cold–Induced Pain in Normal Subjects", Pain (1989) 39:231–6**.

Johnson, MI, et al. "An In–Depth Study of Long Term Users of Transcutaneous Electrical Nerve Stimulation (TENS). Implications for Clinical Use of TENS", Pain (1991) 44:221–9**.

Katims, J.J. et al., "Transcutaneous Nerve Stimulation. Frequency and Waveform Specificity in Humans", Appl. Neurophysiol (1986) 49:86–91**.

Leem, J., "Electrosphysiological evidence for the antinociceptive effect of transcutaneous electrical stimulation on mechanically evoked responsiveness of dorsal horn neurons in neuropathic rats", Neuroscience Letters (1995) 192:197–200**.

Liss S., Liss B., "Physiological and Therapeutic Effects of High Frequency Electrical Pulses", Integr.Physio.Behav. Sci. (Apr.–Jun. 1996) 31:88–94.

Marchand, S., et al., "Modulation of Heat Pain Perception by High Frequency Transcutaneous Electrical Nerve Stimulation (TENS)", Clin.J.Pain (1991) 7:122–9**.

Moreno–Aranda J., "Electrical Parameters for over-the-skin muscle stimulation", J. Biomechanics (1981) 14:9, 579–585**.

Moreno–Aranda J., Seireg, A., "Investigation of over-the-skin electrical stimulation parameters for different normal muscles and subjects", J. Biomechanics (1981) 14:9; 587–593**.

O'Brien, WJ, "Effect of Transcutaneous Electrical Nerve Stimulation on Human Blood B–Endorphin Levels", Physical Therapy (Sep. 1984) 64:1367–1374.

Ordog, G., "Transcutaneous Electrical Nerve Stimulation Versus Oral Analgesic: A Randomized Double–Blind Controlled Study in Acute Traumatic Pain", American Journal of Emergency Medicine (Jan. 1987) 5:1, 6–10.

Rooney, J.G., et al., "Effect of Variation in the Burst and Carrier Frequency Modes of Neuromuscular Electrical Stimulation on Pain Perception of Healthy Subjects", Phys. Ther. (Nov. 1992) 72:11, 800–808.

Sluka, K.A., "Treatment with Either High or Low Frequency TENS Reduces the Secondary Hyperalgesia Observed After Injection of Kaolin and Carrageenan into the Knee Joint", Pain (1998) 77:97–102.

Somers. D.L., "High–Frequency Transcutaneous Electrical Nerve Stimulation Alters Thermal but not Mechanical Allodynia Following Chronic Constriction Injury of the Rat Sciatic Nerve", Arch.Phys.Med.Rehabil. (Nov. 1998) 79:1370–6.

Van Doren, CL, "Contours of Equal Perceived Amplitude and Equal Perceived Frequency for Electrocutaneous Stimuli", Percept.Phychophys. (1997) 59:613–22**.

Ahmed et al., "Percutaneous Electrical Nerve Stimulation (PENS): A Complementary Therapy for the Management of Pain Secondary to Bony Metastasis," Clinical Journal of Pain 14:320–3 (Dec. 1998).

Ahmed et al., "Percutaneous Electrical Nerve Stimulation: An Alternative to Antiviral Drugs for Herpes Zoster," Anesth. Analg. 87:911–4 (Oct. 1998).

Ballegard et al., "Acupuncture and Transcutaneous Electric Nerve Stimulation in the Treatment of Pain Associated with Chronic Pancreatitis," Scan. J. Gastroenterol. 20:1249–54 (Dec. 1985).

Balogun et al., "The effects of acupuncture, electroneedling and transcutaneous electrical stimulation therapies on peripheral haemodynamic functioning," Disability and Rehab. 20:41–8 (Feb. 1998).

Bushnell et al., "Electrical stimulation of peripheral and central pathways for the relief of musculoskeletal pain," Can.J.Physiol.Pharmacol. 69:697–703 (May 1991).

Cheng et al., "Electrotherapy of Chronic Musculoskeletal Pain: Comparison of Electroacupuncture and Acupuncture–Like Transcutaneous Electrical Nerve Stimulation," Clin.J-.Pain 2:143–9 (1987).

Cheng et al., "Electroactupuncture analgesia could be mediated by at least two pain–relieving mechanisms: endorphin and non–endorphin systems," Life Sciences 25:1957–62 (Dec. 3, 1979).

Cheng et al., "Electroacupuncture elevates blood cortisol levels in naive horses; sham treatment has no effect," Intern.J.Neuroscience 10:95–7 (1980/no month listed).

Gadsby et al., "Nerve stimulation for low back pain–a review," Nursing Standard 11:32–3 (Jul. 16, 1997).

Ghoname et al., "Percutaneous electrical nerve stimulation: an alternative to TENS in the management of sciatica," Pain 83:193–9 (Nov. 1999).

Ghoname et al., "Percutaneous Electrical Nerve Stimulation for Low Back Pain," JAMA 281:818–23 (Mar. 3, 1999).

Ghoname et al., "The Effect of Stimulus Frequency on the Analgesic Response to Percutaneous Electrical Nerve Stimulation in Patients with Chronic Low Back Pain," Anesth.Analg. 88:841–6 (Apr. 1999).

Landau et al., "Neuromodulation Techniques for Medically Refractory Chronic Pain," Annu.Rev.Med. 44:279–87 (1993)/no month listed (annual publication).

Lehmann et al., "Efficacy of Electroacupuncture and TENS in the Rehabilitation of Chronic Low Back Pain Patients," Pain 26:277–90 (Sep. 1986).

Omura, "Basic electrical parameters for safe and effective electro–therapeutics [electroacupuncture. TES, TENMS (or TEMS), TENS and electro–magnetic field stimulation with or without drug field] for pain, neuromuscular skeletal problems, and circulatory disturbances," Acupuncture & Electro–Therapeutics Res. 12:201–25 (1987)/no month listed.

Omura, "Electrical parameters for safe and effective electro–acupuncture and transcutaneous electrical stimulation: Threshold potentials for tingling, muscle contraction and pain; and how to prevent adverse effects of electro–therapy," Acupuncture & Electro–Therapeutics Res. 10:335–7 (1985)/ no month listed.

Romita et al., "Parametric Studies on Electroacupuncture–Like Stimulation in a Rat Model: Effects of Intesity, Frequency, and Duration of Stimulation on Evoked Antinociception," Brain Res.Bull. 42:289–96 (1997)/no month listed.

Ulett et al., "Elecroacupuncture: Mechanisms and Clinical Application," Biol.Psych. 44:129–38 (Jul. 15, 1998).

Radionics RFG–3C product brochure (1997).

Balogun et al., "The effects of ramp time on sensory, motor and tolerance thresholds during exogenous electrical stimulation," Journal of Sports Medicine and Physical Fitness. (Dec. 1991) vol. 3, No. 4, pp. 521–525.

BD Microtainer Safety Flow Lancet –Product Number 366356. BD catalog 1997–2000, http://catalog.bd.com/sc-tipts/OBDsheet.exe (accessed Aug. 7, 2001).

BD Vacutainer Safety Glide Blood Collection Assembly. Quick Reference Card (Oct. 1999).

Cramp AF et al., "The Effect of High and Low Frequency Transcutaneous Electrical Nerve Stimulation Upon Cutaneous Blood Flow and Skin Temperature in Healthy Subjects", Clin. Physio. (Mar. 2000) vol. 20, No. 2, pp. 150–157 Blackwell Science.

Galletti S.P. et al., Highlights concerning low frequency–high intensity TENS (review). Minerva Stomatol (Sep. 1995) vol. 44, No. 9, pp. 421–429 (English Summary attached).

Ghoname et al., "Does the Stimulus Frequency Affect the Analgesic Response to Electrical Stimulation?", Anesth. Analg. (Nov. 1999) 88:S210.

Ghoname et al., "The Effect of the Duration of Electrical Stimulation on the Analgesic Response", Anesth. Analg. (Jan. 1999) 88:S211.

Innovative Healthcare: Electrotherapy Pain & Rehabilitation Product Solutions from Rehabilicare. [Includes product description of SporTX and Ortho DX]. (accessed Aug. 7, 2001). www.mvpdesign.com.

Intelect Legend Stim Clinical Reference Manual, vol. 4 Intelect Legend Series, Chattanooga Group, Inc., (Jul. 2000) 25 pages.

SMP–plus. The Pain Relief Solution for Hard to Treat Patients, Rehabilicare, Inc. (Aug. 1999) 2 pgs.

Starobinets, M., Volkova, L., [Analgesic Effect of High–Frequency and Acupuncture–Like Trancutaneous Electric Stimulation of Nerve Fibers in Spinal Osteochondritis]. Zh Nevropatol Psikhiatr Im S. S. Korsakova (Feb. 1985) 85–350–4 (English Summary attached).

White, P.F. et al., "Percutaneous Neuromodulation Therapy: Does the Location of Electrical Stimulation Effect the Acute Analgesic Response?", Anesth. Analg. (Oct. 2000) 91:1–6.

White, P.F. et al., "The Effect of Montage on the Analgesic Response to Percutaneous Neuromodulation Therapy", Anesth. Analg. (Feb. 2001) 92:483–7.

User's Manual for the Empi EPIX VT TENS Device, Empi, Inc. (Sep. 1998) 22 pgs.

* cited by examiner

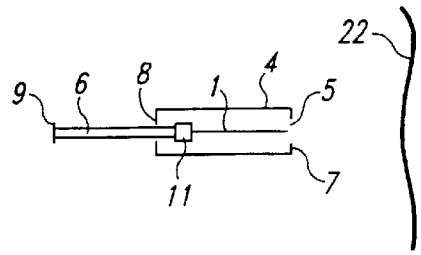
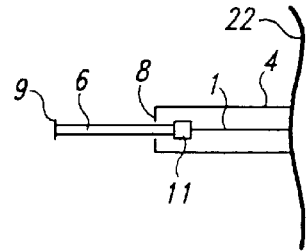
Fig. 1A          Fig. 1B
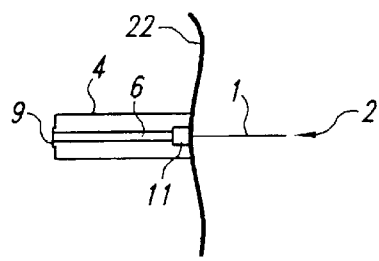
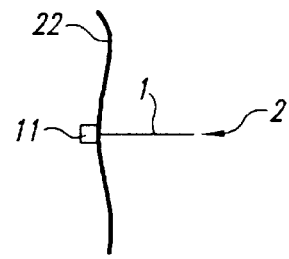
Fig. 1C          Fig. 1D
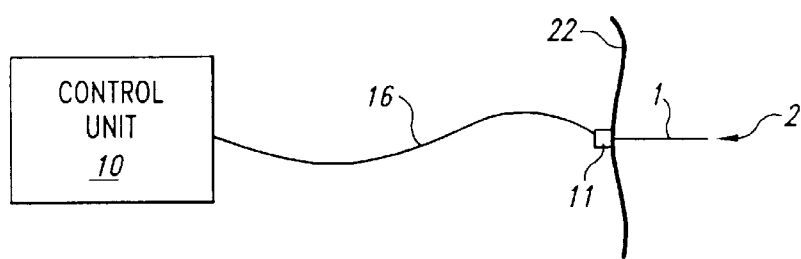
Fig. 1E
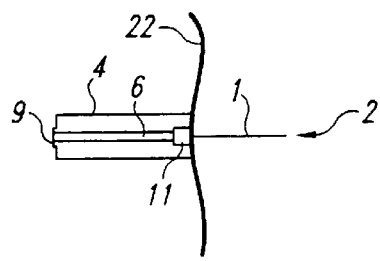
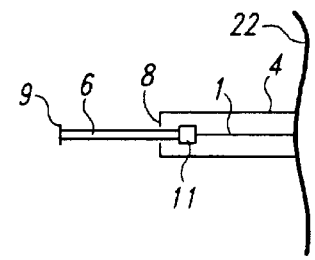
Fig. 1F          Fig. 1G

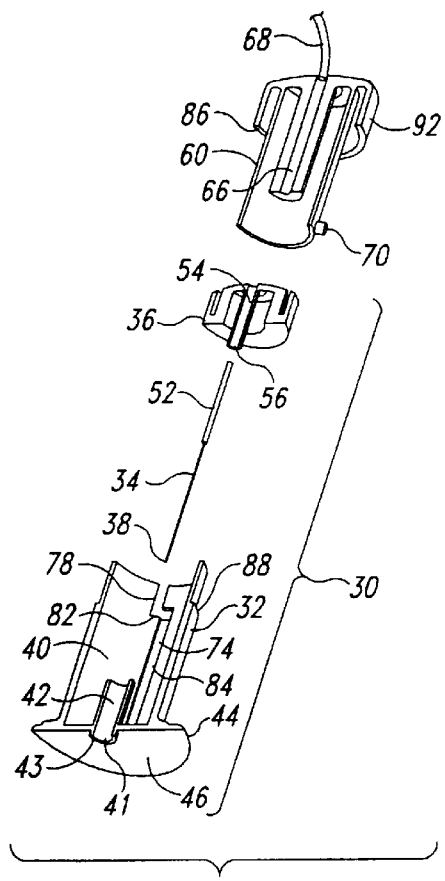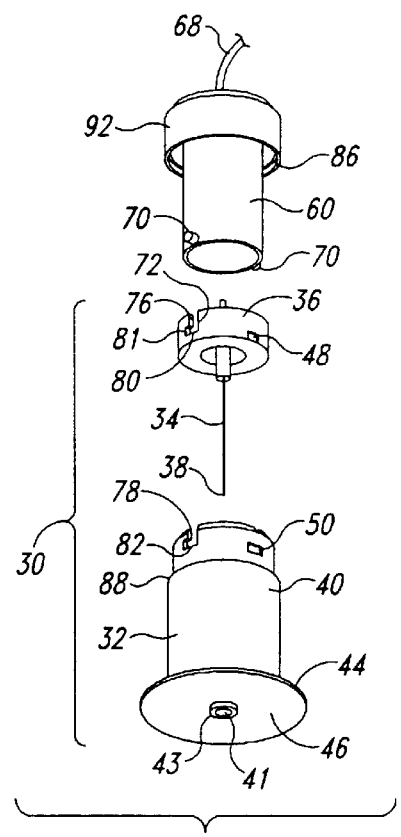
Fig. 4    Fig. 5
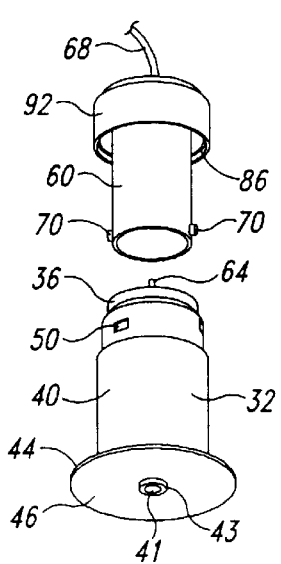
Fig. 6

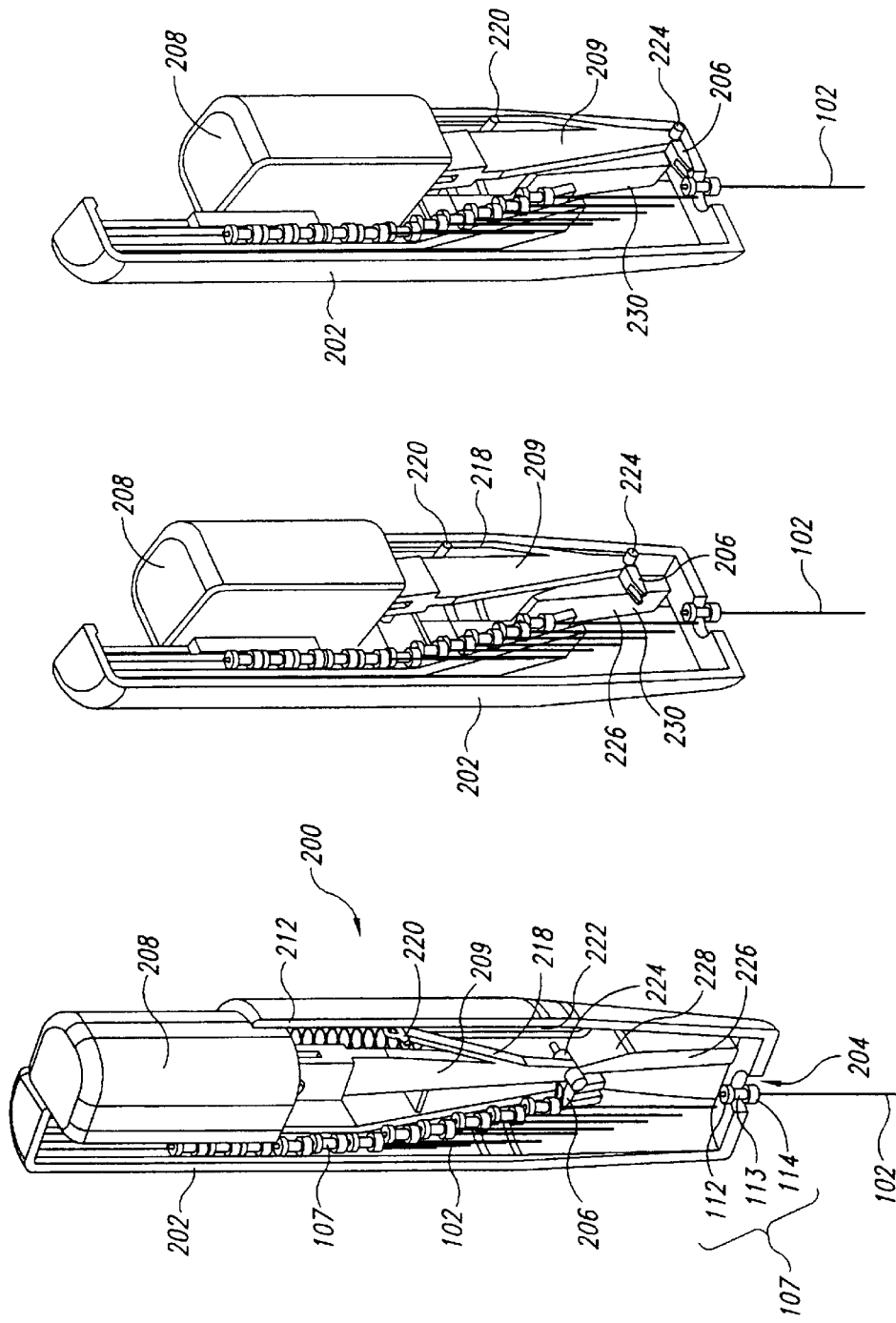

PERCUTANEOUS ELECTRICAL THERAPY SYSTEM WITH ELECTRODE ENTRY ANGLE CONTROL

BACKGROUND OF THE INVENTION

This invention relates generally to percutaneous electrical therapy systems for medical use. In particular, the invention relates to a percutaneous electrode entry angle control assembly and method for use with an electrical therapy system.

Electrical therapy has long been used in medicine to treat pain and other conditions. For example, transcutaneous electrical nerve stimulation (TENS) systems deliver electrical energy through electrode patches placed on the surface of a patient's skin to treat pain in tissue beneath and around the location of the patches. The efficacy of TENS systems in alleviating pain is questionable at best, however.

More recently, a technique in which electrodes are placed through the patient's skin into the target tissue has been proposed. Percutaneous Neuromodulation Therapy ("PNT") (also sometimes called Percutaneous Electrical Nerve Stimulation or "PENS") using percutaneously placed electrodes achieves significantly better pain relief results than TENS treatments using skin surface electrodes. This therapy is described in Ghoname et al., "Percutaneous Electrical Nerve Stimulation for Low Back Pain," JAMA 281:818–23 (1999); Ghoname et al., "The Effect of Stimulus Frequency on the Analgesic Response to Percutaneous Electrical Nerve Stimulation in Patients with Chronic Low Back Pain," Anesth. Analg. 88:841–6 (1999); Ahmed et al., "Percutaneous Electrical Nerve Stimulation (PENS): A Complementary Therapy for the Management of Pain Secondary to Bony Metastasis," Clinical Journal of Pain 14:320–3 (1998); and Ahmed et al., "Percutaneous Electrical Nerve Stimulation: An Alternative to Antiviral Drugs for Herpes Zoster," Anesth. Analg. 87:911–4 (1998). The contents of these references are incorporated herein by reference.

Thus far, PNT practitioners have used percutaneously placed acupuncture needles attached to waveform generators via cables and alligator clips to deliver the therapy to the patient. This arrangement and design of electrodes and generator is far from optimal. For example, the prior art has not addressed the issue of how to control the entry angle of percutaneous electrodes used in PNT and other electrical therapies. It is therefore an object of this invention to provide electrode entry angle control in percutaneous electrical therapy systems.

It is a further object of this invention to provide a percutaneous electrical therapy system having electrodes and electrode assemblies that are safe, efficacious, inexpensive and easy to use.

Other objects of the invention will be apparent from the description of the preferred embodiments.

SUMMARY OF THE INVENTION

The invention is a percutaneous electrical therapy system with electrode angle of entry control. In a preferred embodiment, the system includes a control unit; an electrode electrically connectable to the control unit to deliver electrical therapy to a patient, the electrode having a sharp point at a distal end adapted to be inserted into a patient's tissue; and an electrode angle of insertion assembly controlling the electrode's angle of entry into the patient's tissue. The electrode angle of insertion assembly preferably includes a housing supporting the electrode during insertion of the electrode into a patient's tissue. In some embodiments of the invention, the housing has a distal face adapted to be placed on the patient to control the angle between the housing and the patient. The housing may also have an aperture in its distal face, the aperture being adapted to surround at least a portion of the electrode during insertion of the electrode into the patient's tissue. In some embodiments, the distal face has a diameter greater than the housing's diameter. Also, in some embodiments of this invention the electrode is adapted to move with respect to the housing during insertion of the electrode into the patient's tissue.

There may also be a mechanical connection between the electrode and the housing during insertion of the electrode into the patient's tissue. In some embodiments, the electrode and the housing are adapted to remain mechanically connected during application of electrical therapy to the patient. Also, the housing may be adapted to be separated from the electrode after insertion of the electrode into the patient's tissue but before application of electrical therapy to the patient. The electrode angle of insertion assembly may also include a housing alignment member disposed on the patient's tissue and adapted to mechanically interact with the housing to align the housing with respect to the patient's tissue, such as a patch attached to the patient's tissue. In the patch embodiment, the patch may be an annular member adapted to mate with the housing and to surround the electrode during insertion of the electrode into the patient's tissue.

In some embodiments, the electrode angle of insertion assembly has an electrode actuator movable within the housing, the electrode actuator being adapted to move the sharp point of the electrode into the patient's tissue.

Also, in some embodiments the system also includes an electrode insertion pain reducer adapted to reduce pain experienced by the patient during insertion of the sharp point of the electrode into the patient's tissue.

The invention also includes the percutaneous electrode and electrode angle of insertion assembly described above apart from the control unit.

The invention is also a method of performing percutaneous electrical therapy including the steps of: aligning an electrode assembly housing with a patient's tissue; inserting a sharp point of an electrode into the patient's tissue, the housing supporting the electrode during insertion to control the electrode's angle of insertion; and applying an electrical signal to the electrode from a control unit. In some embodiments, the aligning step includes the step of placing a distal face of the housing against the patient's tissue. The placing step may include the step of attaching the distal face of the electrode assembly housing to the patient's tissue.

In some embodiments, the method includes the steps of placing a housing alignment member on the patient's tissue, wherein the aligning step comprising interacting the housing with the housing alignment member.

The invention is described in further detail below with reference to the drawings.

Brief Description of the Drawings

FIGS. 1A–G are schematic renderings of a percutaneous electrical therapy system according to one embodiment of this invention.

FIG. 1A shows electrode and angle of insertion assemblies wherein the electrode is in an undeployed and uninserted state.

FIG. 1B shows the electrode and angle of insertion assemblies of FIG. 1A during deployment but prior to insertion of the electrode into a patient's tissue.

FIG. 1C shows the electrode and angle of insertion assemblies of FIG. 1A during deployment and insertion of the electrode into the patient's tissue.

FIG. 1D shows the electrode of FIG. 1A inserted into the patient's tissue.

FIG. 1E shows the electrode of FIG. 1A attached to a control unit to provide percutaneous electrical therapy.

FIG. 1F shows the electrode and angle of insertion assemblies of FIG. 1A during undeployment but prior to removing the electrode from the patient's tissue.

FIG. 1G shows the electrode and sharp point protection assemblies of FIG. 1A during undeployment and after removing the electrode from the patient's tissue.

FIG. 2A shows a percutaneous electrical therapy system with electrode and angle of insertion assemblies wherein the electrode is in an undeployed and uninserted state.

FIG. 2B shows the percutaneous electrical therapy system of FIG. 2A during deployment, but prior to insertion, of the electrode.

FIG. 2C shows the percutaneous electrical therapy system of FIG. 2A with the electrode in a deployed and inserted state.

FIG. 2D shows the percutaneous electrical therapy system of FIG. 2A during undeployment of the electrode.

FIG. 2E shows the percutaneous electrical therapy system of FIG. 2A after the electrode has been undeployed.

FIG. 4 is an exploded sectional view of an electrode and angle of insertion assembly according to yet another embodiment of this invention.

FIG. 5 is a partially exploded elevational view of the embodiment of FIG. 4.

FIG. 6 is an elevational view of the embodiment of FIG. 4 showing the electrode and angle of insertion assemblies and an actuator tool.

FIG. 23 is a partial sectional view of an electrode remover and angle of insertion assembly according to yet another embodiment of the invention prior to removal of an electrode.

FIG. 24 is a partial sectional view of the electrode remover and angle of insertion assembly of FIG. 23 partially actuated but prior to removal of an electrode.

FIG. 25 is a partial sectional view of the electrode remover and angle of insertion assembly of FIG. 23 partially actuated but prior to removal of an electrode.

DETAILED DESCRIPTION OF THE PREFERRED EMBODIMENTS

Figure 2A:
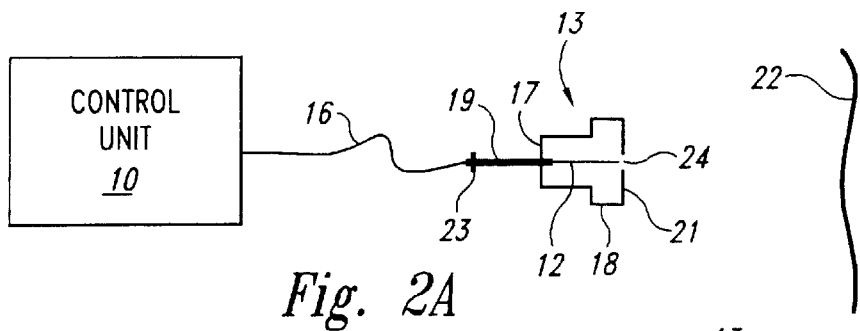
FIGS. 2A–E are schematic renderings of a percutaneous electrical therapy system according to another embodiment of this invention.

Percutaneous electrical therapy systems, such as PNT systems, deliver electric current to a region of a patient's tissue through electrodes that pierce the skin covering the tissue. The electric current is generated by a control unit external to the patient and typically has particular waveform characteristics such as frequency, amplitude and pulse width. Depending on the treatment or therapy being delivered, there may be one electrode containing both a cathode and an anode or a plurality of electrodes with at least one serving as a cathode and at least one serving as an anode.

The electrode has a sharp point not only to facilitate insertion through the patient's skin but also to enhance local current density during treatment. The placement and location of the electrode's point is therefore an important aspect of the therapy. The angle at which the electrode enters the patient's tissue helps determine where the electrode's point will end up. This invention therefore provides an electrode angle of entry assembly for use with a percutaneous electrical therapy system.

FIGS. 1A–G are block diagrams showing deployment and use of one embodiment of this percutaneous electrical therapy system and electrode assembly invention. As shown in FIGS. 1A and 1B, the system includes an electrode 1 having a sharp point 2 at its distal end and a housing 4 surrounding at least the electrode's sharp point 2 when the electrode is in its undeployed and uninserted states. The undeployed and uninserted states include pre-deployment and post-deployment states of the electrode. Housing 4 has an aperture 5 at its distal end. An actuator 6 interacts with a handle 11 at the proximal end of electrode 2 as shown.

Deployment of the electrode assembly includes the steps taken to place the electrode assembly in proper position and condition for use in electrical therapy. FIG. 1A shows the electrode assembly in an undeployed (pre-deployed) state. During deployment, the distal face 7 of housing 4 is placed against a patient's skin 22, as shown in FIG. 1B. This action supports housing 4 with respect to the patient's skin, thereby controlling the angle between the housing and the patient's skin. Electrode 2 is then inserted through aperture 5 into the tissue underlying the patient's skin by moving actuator 6 distally, as shown in FIG. 1C. As it moves, actuator 6—and therefore electrode 2—is supported by housing 4 to control the electrode's angle of entry into the patient's tissue.

Actuator 6 may have an optional limit stop 9 element cooperating with a limit stop area 8 of housing 4 to limit distal motion of actuator 6 and to control the depth of insertion of sharp point 2 of electrode 1. In a preferred embodiment of the invention, for example, where the electrical therapy system is used to provide percutaneous neuromodulation therapy, the predetermined electrode depth is 3 cm. Other electrode depths may be used, of course, depending on the intended application and therapy.

After insertion, housing 4 and actuator 6 (which have heretofore acted as an electrode introducer) are preferably removed, as shown in FIG. 1D. Electrode 1 is connected to a control unit 10 via a conductor or cable 16. For use with PNT, control unit 10 preferably supplies a current-regulated and current-balanced waveform with an amplitude of up to approximately 20 mA, frequency between approximately 4 Hz and 50 Hz, and pulse width of between approximately 50 $\mu$sec and 1 msec. Other electrical waveforms having other parameters may be used, of course, depending on the therapy to be provided. Also, while FIG. 1E shows only one electrode connected to the control unit, it should be understood that a plurality of electrodes may be connected to a single control unit, as called for by the desired electrical stimulation treatment.

After completion of the electrical therapy, the electrode assembly is undeployed. In this embodiment, as shown in FIG. 1F, the aperture 5 of housing 4 is placed over the handle portion 11 of electrode 1. Housing 4 may be the same used to deploy and insert the electrode (i.e., the electrode introducer), or it may be an entirely different assembly (e.g., an electrode remover).

The sharp point 2 of electrode 1 is then drawn into housing 4 of sharp point protection assembly 3 by moving actuator 6 proximally, as shown in FIG. 1G.

FIGS. 2A–E are block diagrams showing another embodiment of our invention. A control unit 10 is connected to an electrode 12 within an electrode assembly 13 via a conductor 16. As above, for use with PNT, control unit 10 preferably supplies a current-regulated and current-balanced waveform with an amplitude of up to approximately 20 mA, frequency between approximately 4 Hz and 50 Hz, and pulse width of between approximately 50 $\mu$sec and 1 msec. As shown in its undeployed state in FIG. 2A and in its uninserted stated in FIG. 2B, the system includes a housing 18 surrounding the sharp point 20 of electrode 12 when the electrode point 20 has not yet been inserted through the patient's skin 22.

Figure 2B:
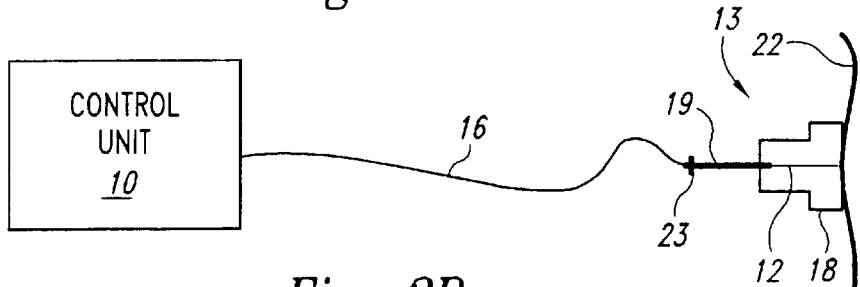
Figure 2C:
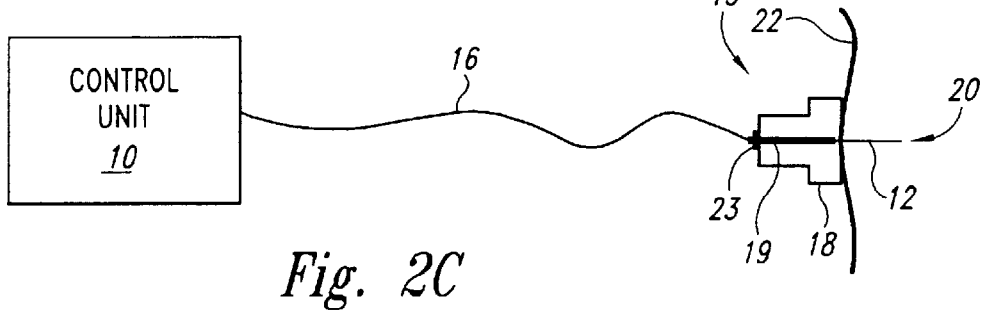

To begin deployment, distal face 21 of housing 18 is placed against the patient's skin 22, as shown in FIG. 2B. As with the previous embodiment, this action supports housing 18 with respect to the patient's skin, thereby controlling the angle between the housing and the patient's skin. The sharp point 20 of electrode 12 is then inserted through an aperture 24 into the tissue underlying the patient's skin by moving an actuator 19 distally, as shown in FIG. 2C. As it moves, actuator 19—and therefore electrode 12—is supported by housing 18 to control the electrode's angle of entry into the patient's tissue.

Actuator 19 may be part of the electrode assembly 13 or a separate component of the system. Actuator 19 may also have an optional limit stop element 23 that cooperates with a limit stop area 17 of housing 18 to limit distal movement of actuator 19, thereby controlling depth of insertion of electrode 12. In a preferred embodiment of the invention, for example, where the electrical stimulation system is used to provide percutaneous neuromodulation therapy, the predetermined electrode depth is approximately 3 cm., although other electrode depths may be used depending on the application. The control unit 10 may then provide the appropriate therapy to the patient through electrode 12 and any other electrodes connected to it.

Figure 2D:
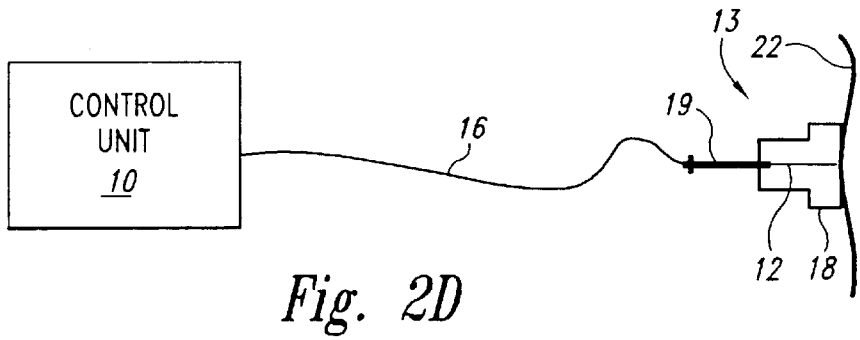
Figure 2E:
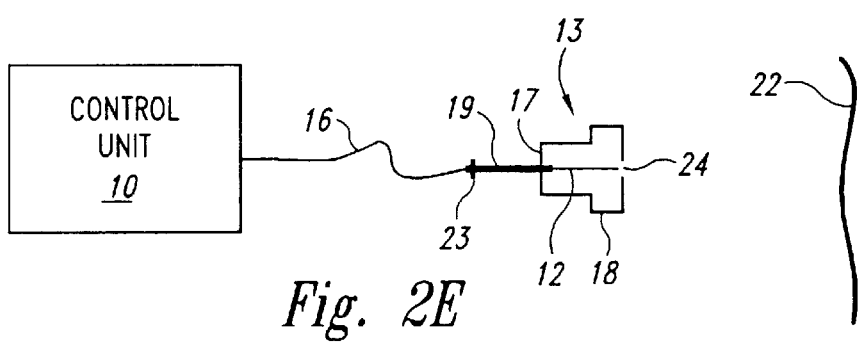

During undeployment, actuator 19 is used to draw electrode 12 back proximally into housing 18. After removal of the electrode from the patient's skin, housing 18 of sharp point protection assembly 14 once again surrounds the sharp point 20 of the now uninserted electrode 12, as shown in FIGS. 2D and 2E. Actuator 19 helps enable this operation to occur without ever exposing the sharp point of the electrode when the sharp point is no longer in the patient. In fact, the operator of the electrode assembly never sees the sharp point of the electrode. Thus, sharp point protection assembly 14 shields the potentially contaminated portion of the undeployed electrode and protects the patient's caregiver or other bystander from unintended contact with the sharp point of the electrode before, during and after electrical therapy.

While FIGS. 2A–E show the electrode connected to the control unit prior to deployment and insertion of the electrode into the patient's skin, the connection between the control unit and the electrode could be made during deployment or after insertion. Also, while FIGS. 2A–E show only one electrode connected to the control unit, it should be understood that a plurality of electrodes may be connected to a single control unit, as called for by the desired electrical stimulation treatment.

Figure 3:
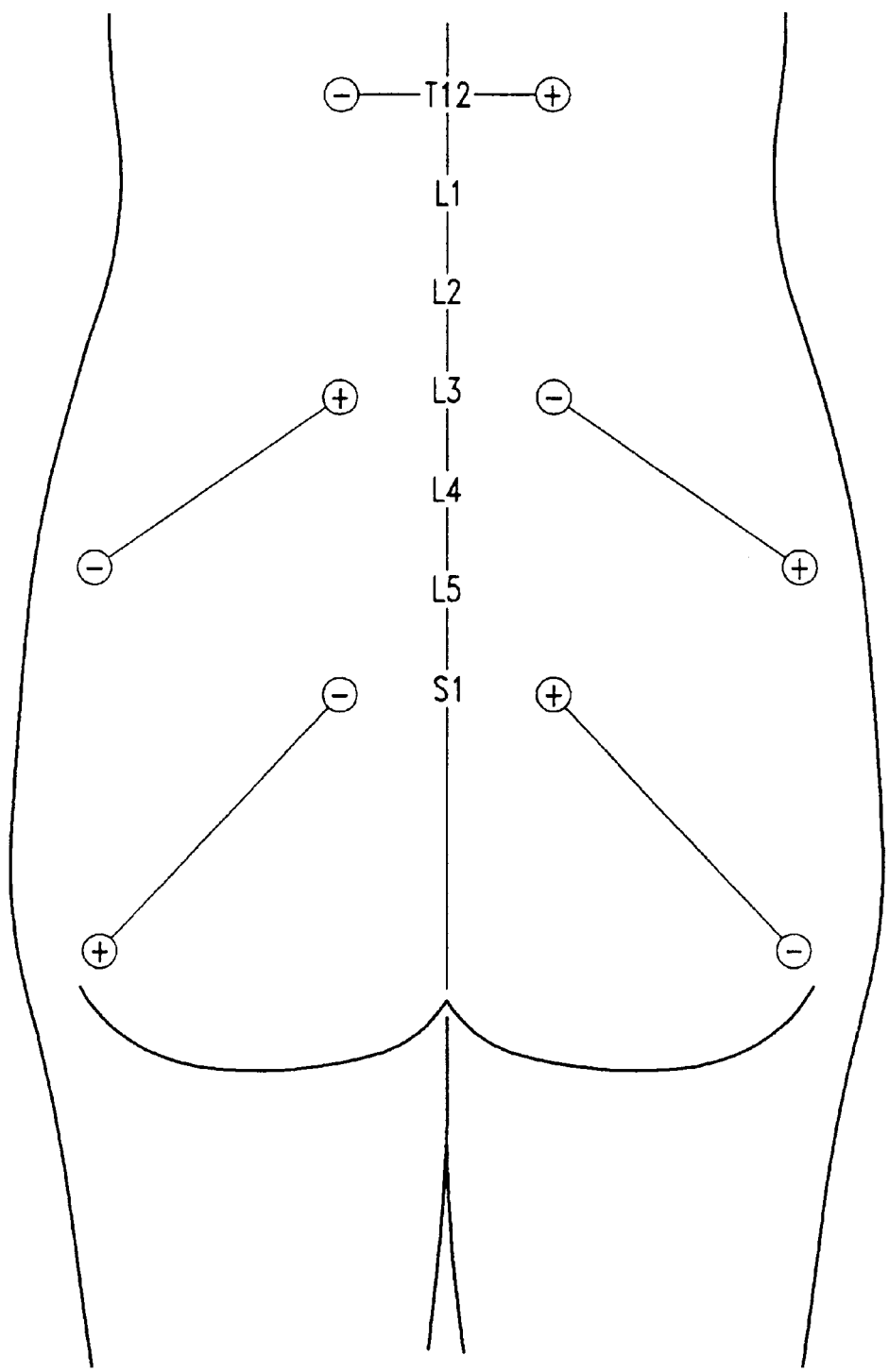
FIG. 3 shows an electrode montage for use in percutaneous neuromodulation therapy to treat low back pain.

To use the percutaneous electrical therapy systems of FIGS. 1A–G and FIGS. 2A–E to treat a patient, one or more electrodes are inserted through the patient's skin into the underlying tissue. As an example, to treat low back pain using PNT with unipolar electrodes, an array or montage such as that shown in FIG. 3 may be used. The "T12"–"S1" designations refer to the patient's vertebrae. The control unit or generator supplies current pulses between pairs of electrodes for durations of a few minutes to several hours, preferably delivering the current-regulated waveform described above. Thirty minute treatments are recommended in the Ghoname et al. low back pain treatment articles.

Additional optional details of the electrode assembly may be found in the following concurrently filed and commonly owned U.S. patent applications, the disclosures of which are incorporated herein by reference: Leonard et al., "Percutaneous Electrical Therapy System Providing Electrode Axial Support;" Leonard et al, "Percutaneous Electrical Therapy System With Electrode Depth Control;" Leonard et al., "Percutaneous Electrical Therapy System With Electrode Position Maintenance;" Leonard et al., "Electrode Introducer For A Percutaneous Electrical Therapy System;" Bishay et al, "Percutaneous Electrical Therapy System For Minimizing Electrode Insertion Discomfort;" Bishay et al., "Electrode Assembly For A Percutaneous Electrical Therapy System;" Leonard et al., "Electrode Remover For A Percutaneous Electrical Therapy System;" and Bishay et al, "Percutaneous Electrical Therapy System With Sharp Point Protection."

FIGS. 4–12 show another embodiment of this invention. An electrode assembly 30 includes a base 32, an electrode 34, and a plunger or actuator 36. Base 32 has a flange or flared end 44 that is adapted to make contact with a patient's skin. Base 32 may be formed from any suitable polymer or metal, such as a high density polyethylene (HDPE). Base 32 is preferably opaque so that the electrode cannot be seen by a needle-shy patient.

Actuator 36 fits within a housing portion 40 of base 32 in a slidable arrangement. A locking assembly is operable to prevent relative movement between actuator 36 and housing 40 of base 32. In this embodiment, the locking assembly of actuator 36 has integrally-formed resilient detents 48 on its exterior cylindrical surface. In the undeployed state of electrode assembly 30, detents 48 mate with a corresponding openings 50 in base 32 to hold actuator 36 and base 32 in place with respect to each other to prevent electrode 34 from moving outside of the protective housing 40 of base 32 and thereby providing sharp point protection. Mechanisms other than the detent and opening arrangement shown here may be used to hold the actuator and base in place may be used without departing from the invention.

In this embodiment, electrode 34 is preferably a 3 cm. long 32 gauge stainless steel needle. Other sizes and materials may be used for electrode 34, of course, without departing from the scope of the invention. Actuator 36 is preferably formed from HDPE as well, although other suitable materials may be used.

Figure 7:
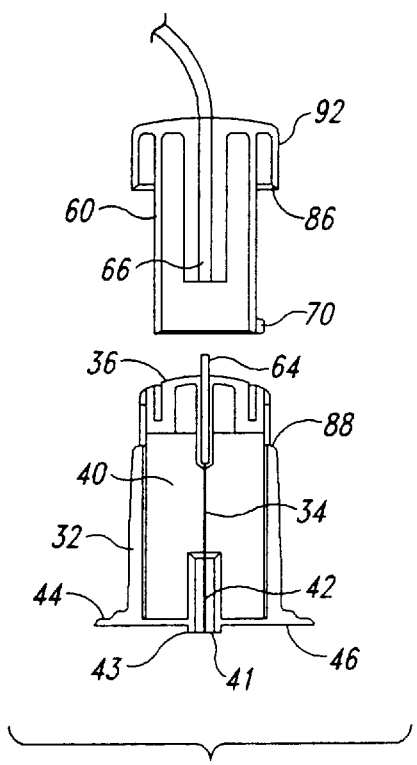
FIG. 7 is a sectional view of the embodiment of FIG. 4 showing the electrode and angle of insertion assemblies and an actuator tool.
Figure 8:
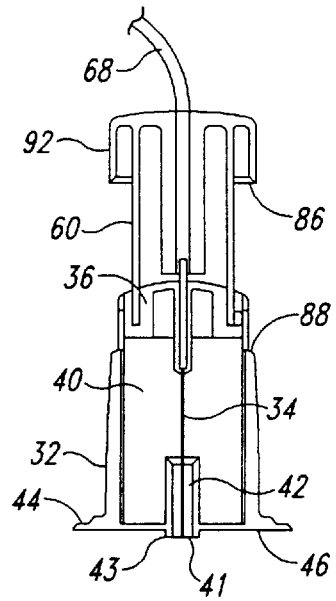
FIG. 8 is a sectional view of the embodiment of FIG. 4 showing the actuator tool in engagement with the electrode and angle of insertion assemblies prior to insertion of the electrode into a patient's tissue.
Figure 9:
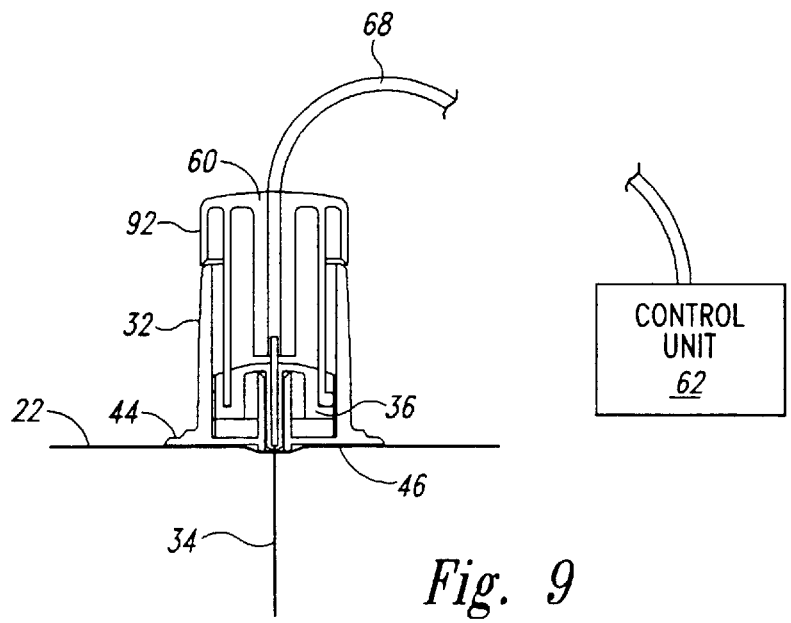
FIG. 9 is a sectional view of the embodiment of FIG. 4 with the electrode in its deployed and inserted state.

Electrode 34 has a larger-diameter handle 52 at its proximal end. Handle 52 fits within a channel 54 formed within actuator 36. Channel 54 has a narrow opening 56 at its distal end whose diameter is slightly larger than the diameter of electrode 34 but narrower than the diameter of handle 52 to hold electrode 34 in place within actuator 36 after initial manufacture and assembly. As shown in FIG. 7, in an undeployed state the sharp point 38 of electrode 34 is disposed within housing portion 40 of base 32, specifically, within a narrow channel 42 of the housing 40.

To deploy one or more electrode assemblies on a patient in order to provide electrical stimulation therapy (such as PNT), the distal surface 46 of flange portion 44 of base 32 is mounted on the desired site on the patient's skin, preferably with a compressible adhesive pad (not shown) surrounding a ring 43 extending downward from surface 46 around an aperture 41 formed at the distal end of channel 42, although other means of attaching base 32 to the patient may be used as appropriate. This action aligns base 32 with respect to the patient's skin. Flange portion 44 of base 32 provides extra stability for the electrode assembly during electrode insertion and use.

An electrical connector and actuator tool 60 is used to insert the electrode and connect the electrode electrically with a control unit 62. Actuator tool 60 and electrode assembly 30 also interact to provide the sharp point protection assembly of this embodiment. When the distal end of actuator tool 60 is placed against the proximal ends of base 32 and actuator 36, the exposed proximal end 64 of electrode handle 52 makes electrical contact with a contact surface 66 within actuator tool 60. Contact surface 66, in turn, is electrically connected to the control unit 62 via a cable or other conductor 68.

Actuator tool 60 has two oppositely disposed pegs 70 extending outward from the distal portion of its cylindrically surface. Pegs 70 mate with two corresponding slots 72 in actuator 36 and with two corresponding grooves 74 in base 32. (The second slot 72 and second groove 74 are each opposite the slot 72 and groove 74, respectively, shown in FIGS. 4 and 5.) When connecting actuator tool 60 to electrode assembly 30, pegs 70 move along longitudinal portions 76 of slots 72 and along longitudinal portions 78 of grooves 74. Concurrently, exposed distal end 64 of electrode handle 52 begins to make sliding contact with contact surface 66 of actuator tool 60 to create the electrical connection between actuator tool 60 and electrode 32.

Clockwise rotation (looking down on the assembly) of actuator tool 60 after pegs 70 reach the end of longitudinal portions 76 and 78 moves pegs 70 into short circumferential portions 80 and 82, respectively, of slots 72 and grooves 74. The length of circumferential portions 80 of slots 72 is less than the length of circumferential portions 82 of grooves 74. Continued movement of pegs 70 along circumferential portions 82 will therefore move pegs 70 against the ends 81 of circumferential slots 80. Further clockwise rotation of actuator tool 60 will cause actuator 36 to rotate clockwise as well, thereby moving detents 48 out of openings 50 and allowing the electrode 34 and actuator 36 to move with respect to base 32.

Second longitudinal portions 84 of grooves 74 are formed in base 32 at the end of circumferential portions 82. Movement of pegs 70 distally along longitudinal portions 84 pushes pegs 70 against the distal edges of circumferential slot portions 80, thereby moving actuator 36 and electrode 34 in a controlled fashion distally toward the patient's skin 22.

As it moves, electrode 34 passes through channel 42, and the sharp point of electrode 34 moves out through aperture 41. Channel 42 and actuator 36 provide axial support to electrode 34 during this forward movement and also, along with the support provided by flange 44, provide entry angle guidance to the electrode. In addition, downward pressure on the patient's skin during electrode deployment compresses the compressible adhesive pad and presses ring 43 against the patient's skin 22, which helps ease electrode entry through the skin and also lessens the insertion pain experienced by the patient.

The alignment of base 32 with respect to the patient's skin and the controlled movement of actuator 36 and electrode 34 within base 32 controls the electrode's angle of entry into the tissue underlying the patient's skin. Distal movement of the electrode and its actuator within base 32 continues until the distal surface 86 of a cylindrical cap portion 92 of actuator tool 60 meets an annular surface 88 of housing 40. At this point, sharp point 38 of electrode 34 has extended a predetermined depth into the tissue underlying the patient's skin. In the preferred embodiment, this predetermined depth is approximately 3 cm., although other electrode depths may be desired depending on the treatment to be performed.

An optional feature of the invention is a deployed electrode holding mechanism. In this embodiment, an interference fit between the inner surface of channel 42 and the outer surface 55 of channel 52 performs this function.

Electrical stimulation treatment may begin once the electrodes have been deployed and inserted. Control unit 62 supplies stimulation current to the electrodes, e.g., in the manner described in the Ghoname et al. articles. The electrical waveform provided by the control unit depends on the application. For example, in an embodiment of a system providing percutaneous neuromodulation therapy, control unit 62 would preferably provide a current-regulated and current-balanced waveform with an amplitude of up to approximately 20 mA, frequency between approximately 4 Hz and 50 Hz, and pulse width of between approximately 50 μsec and 1 msec.

The interaction of actuator tool 60 and base 32 provides stability to electrode 34 and its electrical connection to the control unit during treatment by holding the electrode in place, by providing strain relief for tugging forces on cable 68, and by providing a robust mechanical connection. It should also be noted that the sharp point of the electrode is not exposed to the operator or to any other bystander at any point during deployment and use of the electrode assembly.

After treatment has been completed, the electrode may be removed from the patient. To do so, actuator tool 60 is moved proximally away from the patient. As pegs 70 move proximally along longitudinal portions 84 of grooves 74, pegs 70 push against proximal edges of the actuator's circumferential slot portions 80, thereby moving actuator 36 and electrode 34 proximally as well. When pegs reach the proximal end of longitudinal groove portions 84, the sharp end 38 of electrode 34 is out of the patient and safely inside housing 40 of base 32. Counterclockwise movement of actuator tool 60 moves pegs along circumferential portions 80 and 82 of slot 72 and groove 74, respectively. Since, as discussed above, circumferential portion 80 is shorter than circumferential portion 82, this counterclockwise movement will turn actuator 36 counterclockwise.

At the limit of the counterclockwise movement, detents 48 move back into openings 50 to prevent further movement of the electrode and actuator with respect to base 32. Further distal movement of actuator tool 60 moves pegs 70 distally along longitudinal portions 76 and 78 of slot 72 and groove 74, respectively, to disconnect actuator tool 60 from electrode assembly 30. Base 32 can then be removed from the patient.

Figure 10:
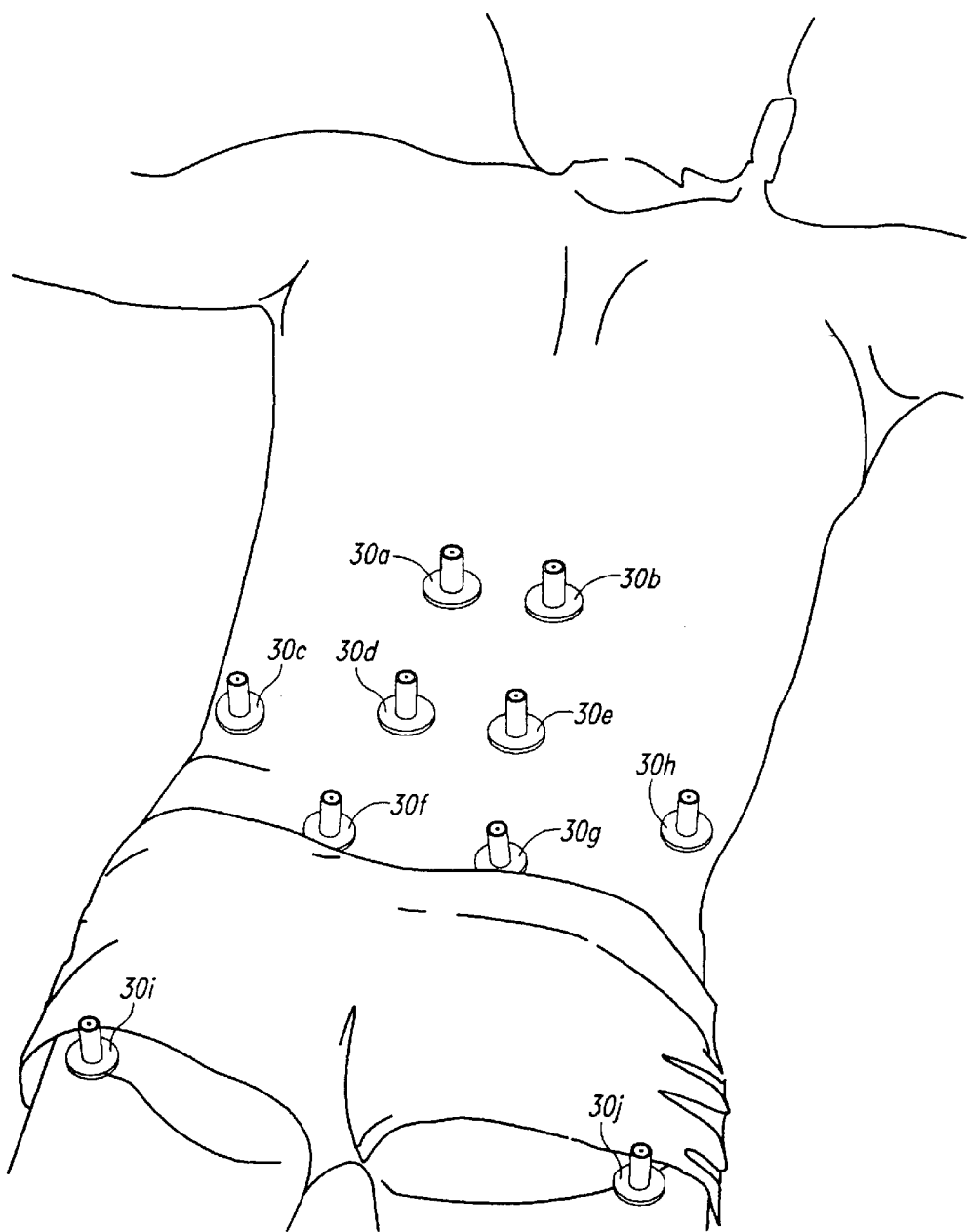
FIG. 10 shows a montage for using the embodiment of FIG. 4 to treat low back pain with the electrodes in a partially deployed but uninserted state.
Figure 11:
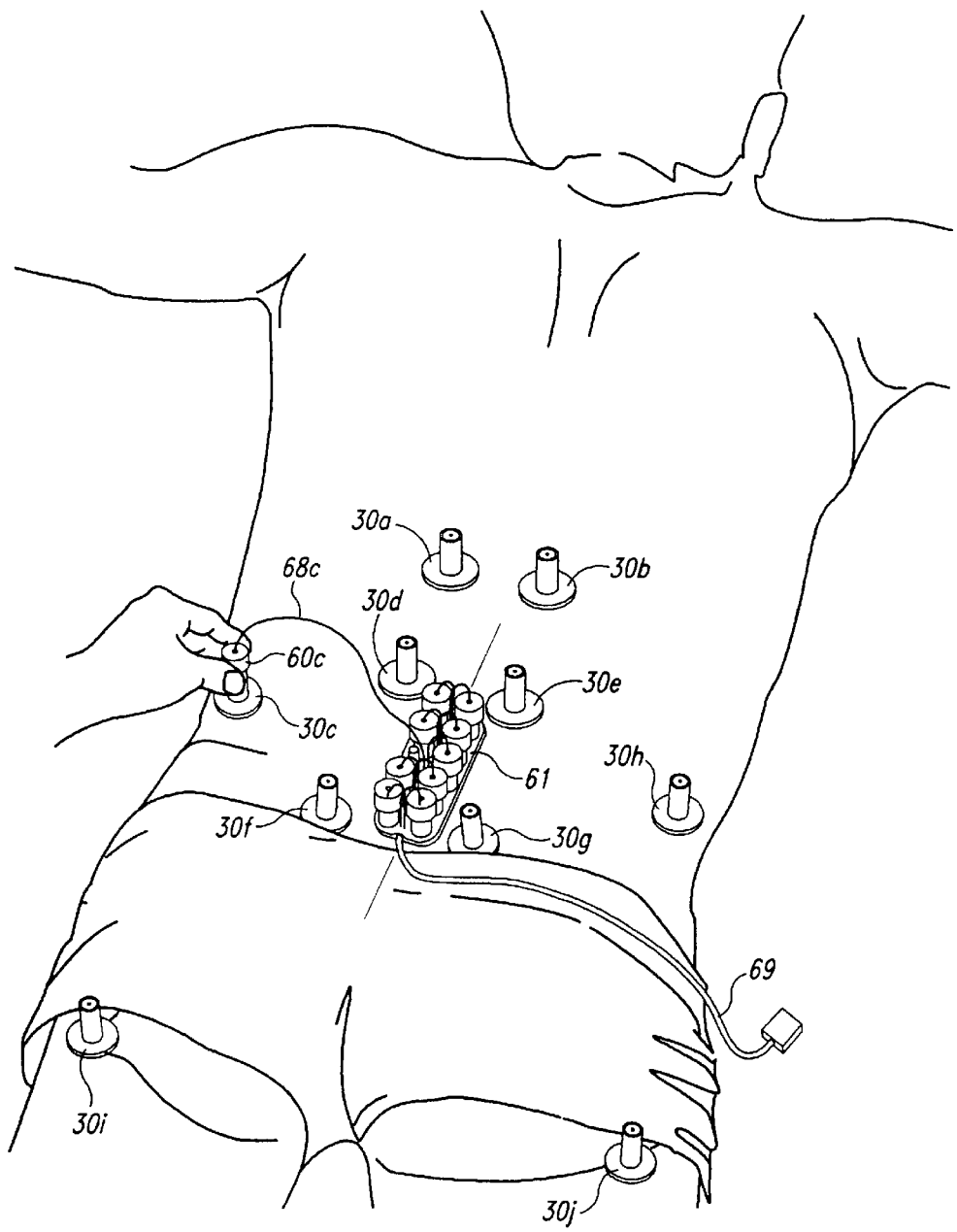
FIG. 11 shows the electrode montage of FIG. 10 at the beginning of the electrode insertion step.
Figure 12:
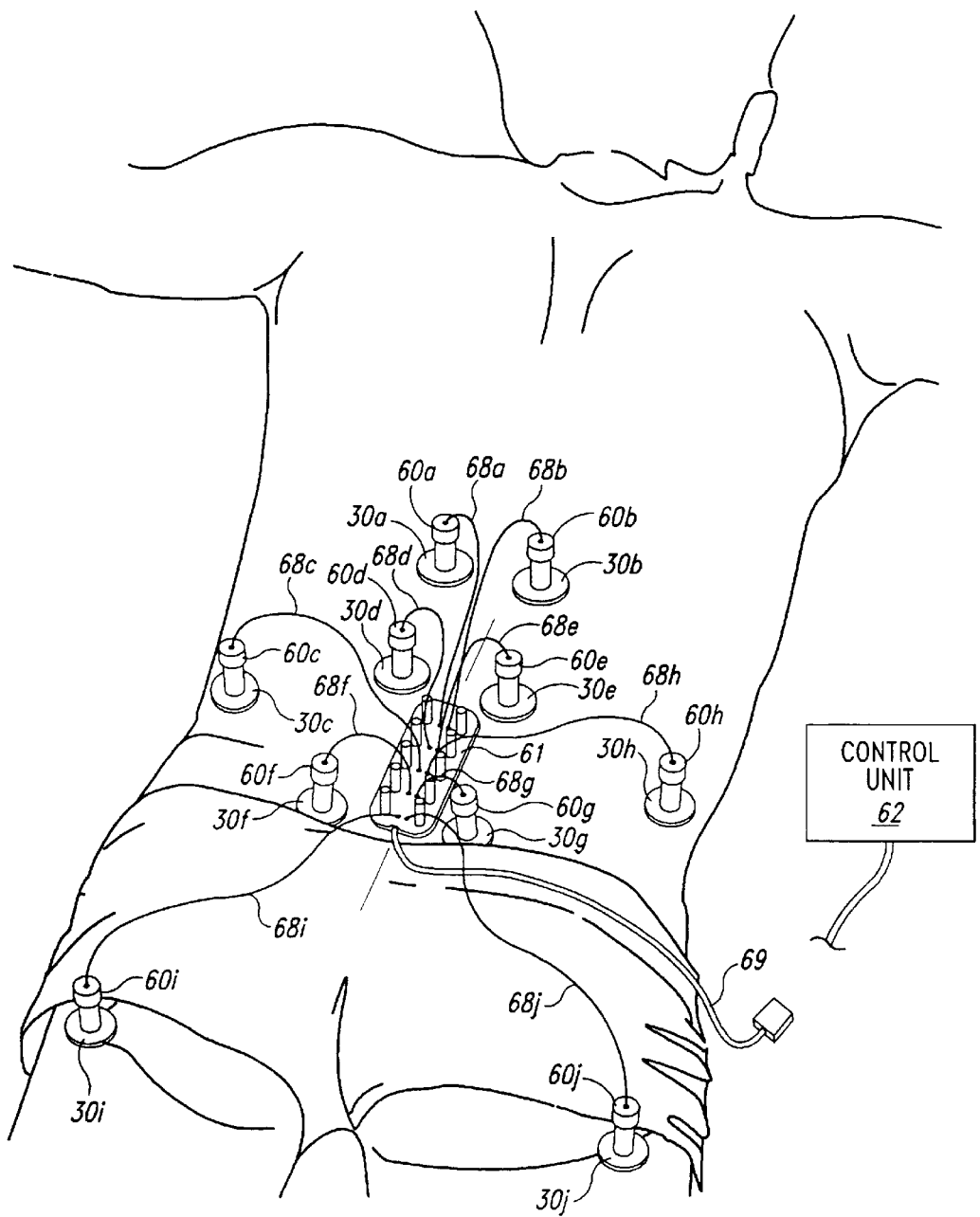
FIG. 12 shows the electrode montage of FIG. 10 with the electrodes deployed, inserted and attached to a control unit to provide electrical therapy to the patient.
Figure 13:
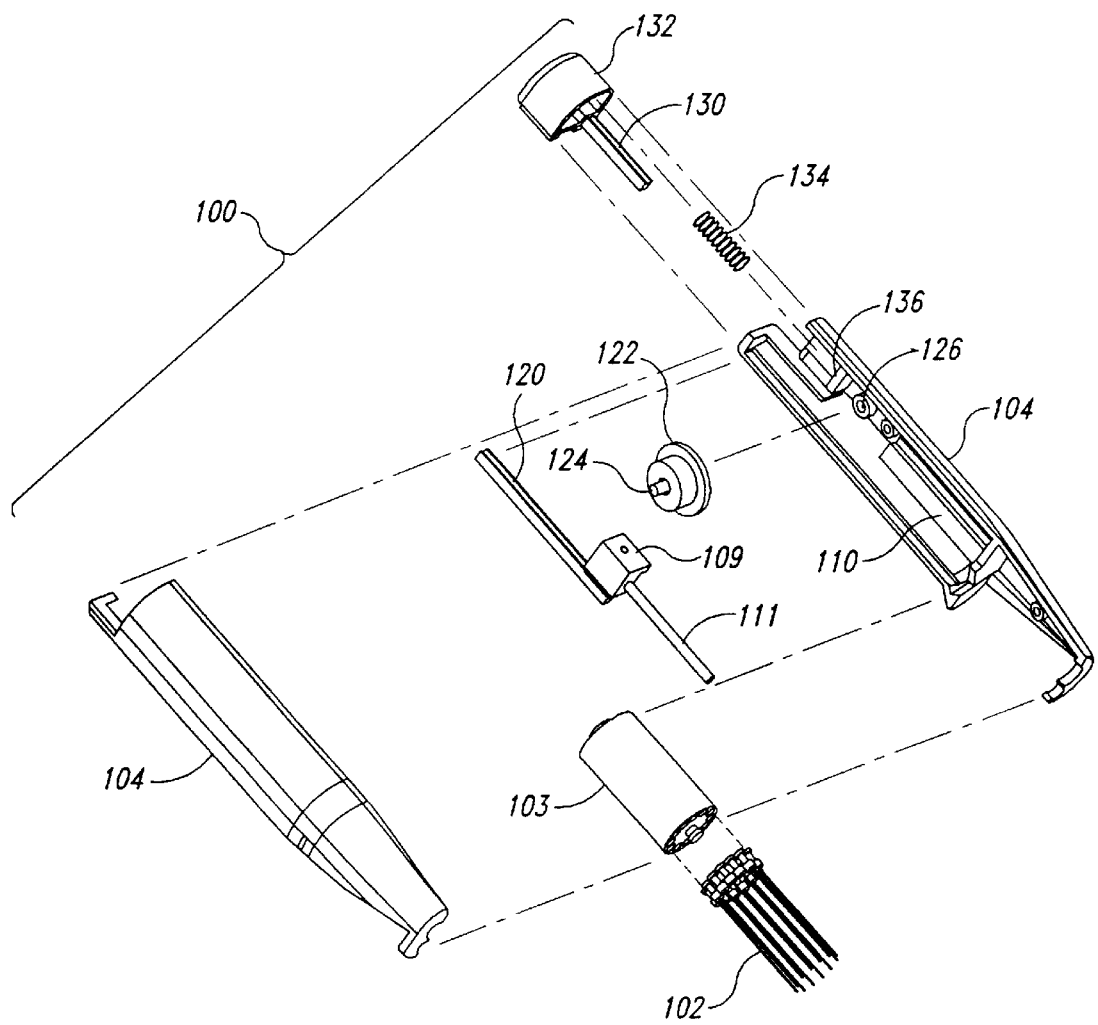
FIG. 13 is an exploded view of an electrode introducer and angle of insertion assembly of yet another embodiment of this invention.

FIGS. 10–12 show the use of the electrode and sharp point protection assemblies of FIGS. 4–9 to treat low back pain using PNT. As shown in FIG. 10, ten electrode assemblies 30*a–j* are arranged in a montage on the patient's back and attached with adhesive. Next, ten actuator tools 60*a–j* are attached to the ten electrode assemblies 30*a–j*. In this example, prior to deployment the actuator tools are mounted on an actuator tool tray 61 that provides electrical communication to a control unit 62 via cable 69. The actuator tools electrically connect with tool tray 61, and thereby to cable 69 and control unit 62, via individual cables 68*a–j*. It should be understood that the tool tray 61 and its electrical connection scheme play no part the invention claimed in the present application FIG. 11 shows the beginning of the electrode insertion process.

Once each electrode assembly has been actuated by its respective actuator tool to insert an electrode into the patient's tissue (as shown in FIG. 12), control unit 62 provides electrical signals to treat the patient. Preferably, half the electrodes (e.g., assemblies 30*b*, 30*d*, 30*g*, 30*h* and 30*i*) are treated as anodes, and the other half as cathodes. In the preferred embodiment, control unit 62 would provide a current-regulated and current-balanced waveform with an amplitude of up to approximately 20 mA, frequency between approximately 4 Hz and 50 Hz, and pulse width of between approximately 50 μsec and 1 msec. to treat the patient's low back pain using PNT.

Another embodiment of the invention is shown in FIGS. 13–28. In this embodiment, an electrode introducer and an alignment member mounted on the patient's skin provide an electrode angle of insertion assembly controlling the electrode's angle of entry into the patient's tissue. In a preferred embodiment of an electrode introducer 100 shown in FIGS. 13–16 and 19–21, introducer 100 is designed to insert multiple electrodes. It should be understood that the principles of this invention could be applied to an introducer designed to hold and insert any number of electrodes.

Twelve electrodes 102 are disposed within a magazine 103 rotatably mounted within a housing 104. In this embodiment, housing 104 is a two-part injection molded polystyrene assembly. As seen best in FIG. 14, magazine 103 rotates about a hub 105 mounted on supports formed in housing 104. A leaf spring 106 mates with one of twelve radial grooves 108 formed in magazine 103 to form a twelve-position ratchet mechanism for rotatable magazine 103 in housing 104.

Figures 14, 15:
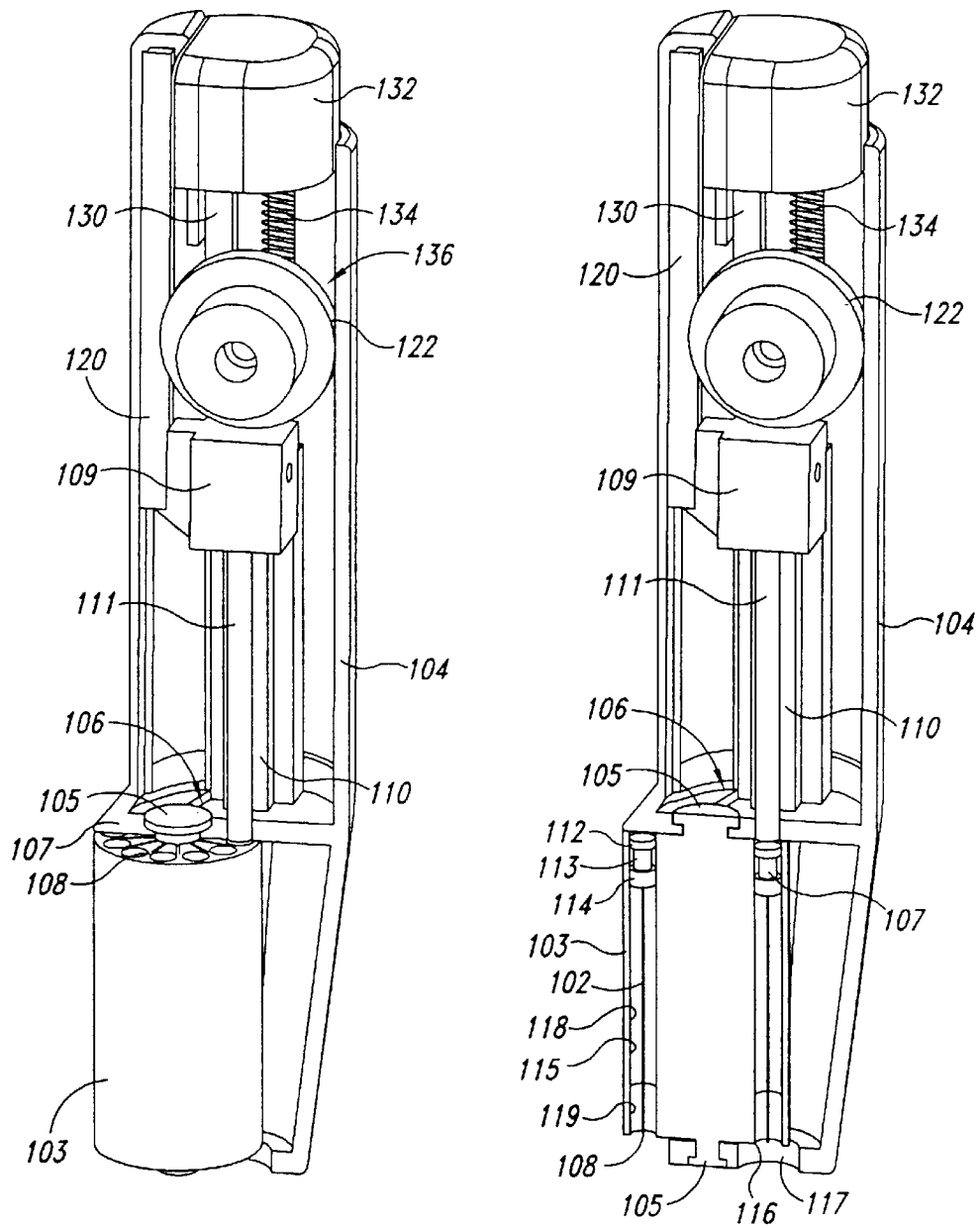
FIG. 14 is a partial sectional view of the introducer and angle of insertion assembly of FIG. 13.
FIG. 15 is a sectional view of the introducer and angle of insertion assembly of FIG. 13.
Figure 16:
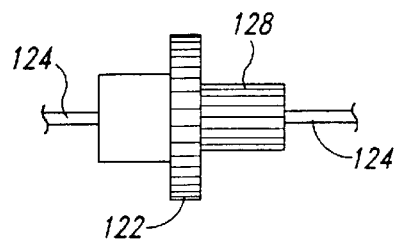
FIG. 16 is an elevational view of gear assemblies of the introducer and angle of insertion assembly of FIG. 13.

Magazine 103 has twelve electrode chambers 115 arranged radially about hub 105. When introducer 100 is completely full, each chamber 115 contains one electrode 102. The diameter of upper portion 118 of chamber 115 is sized to form an interference fit with the wider portions 112 and 114 of electrode handle portion 107 of electrode 102. Lower wide portion 114 of electrode 102 is formed from a compressible material. The diameter of lower portion 119 of chamber 115 is slightly larger so that there is no interference fit between chamber portion 119 and electrode handle 107, for reasons explained below. Each time leaf spring 106 is within a groove 108, the opening 106 of a magazine chamber 115 is lined up with the aperture 117 of introducer 100, as shown in FIGS. 14 and 15.

A slide member 109 is disposed on a rail 110 formed in housing 104. Extending longitudinally downward from slide member 109 is a drive rod 111, and extending longitudinally upward from slide member 109 is a gear rack 120. The teeth of gear rack 120 cooperate with teeth on a rotational gear 122 mounted about a shaft 124 extending into a shaft mount 126 formed in housing 104. A second set of teeth are mounted on a smaller diameter rotational gear 128 (shown more clearly in FIG. 16) which is also mounted about shaft 124. Gears 122 and 128 rotate together about shaft 124.

The teeth of smaller diameter gear 128 mesh with the teeth of a second gear rack 130 extending from a longitudinally-movable actuator 132. A spring 134 mounted between actuator 132 and a spring platform 136 biases actuator 132 away from housing 104.

To deploy the electrode assembly of this embodiment, a flexible and compressible annular patch 140 is placed on the patient's skin at the desired site, preferably with adhesive (not shown). For example, to treat low back pain using PNT, the arrangement or montage shown in FIG. 17 may be used. In this montage, five electrodes serve as cathodes and five serve as anodes.

Figure 20:
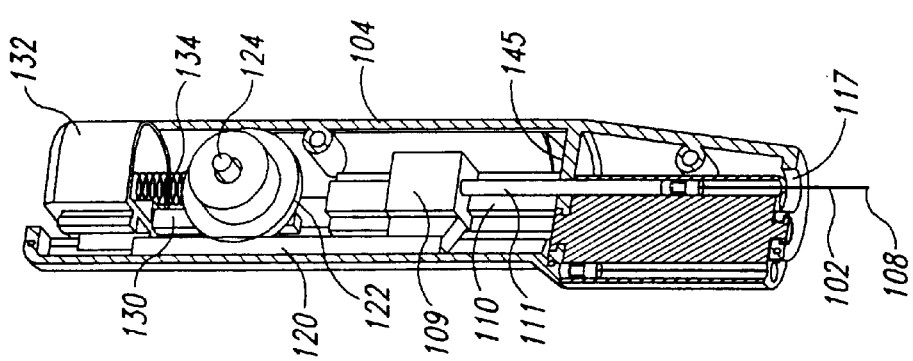
FIG. 20 is a sectional view showing the introducer of FIG. 13 in the process of deploying an electrode, during insertion of the electrode.
Figure 19:
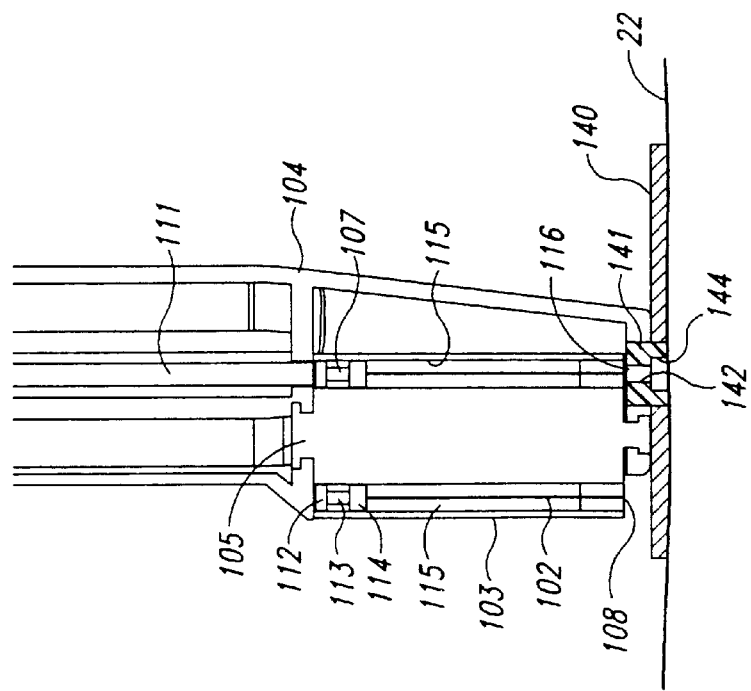
FIG. 19 is a sectional view showing the introducer of FIG. 13 in the process of deploying an electrode, prior to insertion of the electrode.

As shown in FIGS. 19 and 20, patch 140 has an annular rigid member 141 disposed in its center and extending upwardly from it. Rigid member 141 has a smaller diameter opening 142 leading to a larger diameter opening 144. The diameter of opening 142 is slightly smaller than the lower wide portion 114 of the handle portion 107 of electrode 102 and slightly larger than the diameter of the central portion 113 of handle portion 107 of electrode 102.

Figure 18:
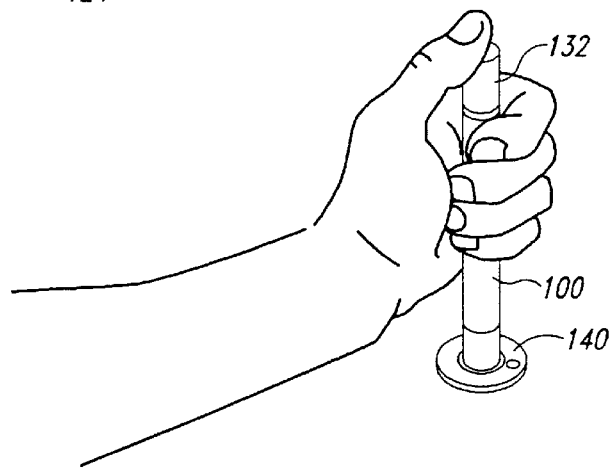
FIG. 18 is an elevational view showing the introducer of FIG. 13 in the process of deploying an electrode.

After the patch 140 is in place, the distal end of introducer 100 is placed against patch 140 so that introducer aperture 117 surrounds the upwardly extending portion of rigid patch member 141, as shown in FIG. 18. This interaction aligns the opening 116 of one of the introducer's magazine chambers 115 with the opening 142 of rigid member 141 and helps control the electrode's angle of entry, as shown in FIG. 19. Downward pressure on introducer 100 compresses patch 140, thereby causing the upper surface of rigid member 141 to engage a lower surface of magazine 103 and pressing rigid member 141 downward into the patient's skin 22. This pressure on the patient's skin around the insertion site minimizes the pain of insertion of the electrode.

Depressing actuator 132 moves gear rack 130 distally, which causes gears 128 and 122 to rotate. Because of the relative diameters and relative tooth counts of gears 128 and 122, gear rack 120 moves longitudinally a much greater distance than the corresponding longitudinal movement of gear rack 130. This feature enables the electrode to be inserted its required distance into the patient's skin using only a comparatively small movement of the operator's thumb. Distal movement of gear rack 120 is guided by the movement of slide member 109 along rail 110.

As slide member 109 moves distally, drive rod 111 moves into a magazine chamber 115 until the distal end of drive rod 111 engages the top surface of the electrode's handle portion 107. As shown in FIG. 20, further distal movement of drive rod 111 pushes electrode 102 downward so that sharp point 108 of electrode 102 leaves the introducer housing and enters the patient's skin 22 and the tissue beneath the skin. Chamber 115 provides axial stability to the electrode 102 during insertion.

When the top portion 112 of electrode handle portion 107 leaves the smaller diameter portion 118 of magazine chamber 115, it enters the larger diameter portion 119 of chamber 115. At this point (shown in FIG. 21), because the diameter of chamber portion 119 is wider than the diameter of the electrode handle 107, the electrode is no longer attached to introducer 100.

Continued downward movement of actuator 132 and drive rod 111 pushes the lower larger diameter portion 114 of electrode handle 107 through the smaller diameter portion 142 of rigid member 141 by compressing handle portion 114. Further downward movement pushes handle portion 114 into the larger diameter portion 144 of rigid member 141 so that the rigid member's smaller diameter portion lies between the larger diameter portions 112 and 114 of the electrode handle 107. This interaction holds the electrode in place in the patient's tissue and helps provides depth control for electrode insertion. In this embodiment, the preferred depth of the electrode's sharp point 108 is approximately 3 cm., although other electrode depths may be desired depending on the treatment to be performed. Slider member 109 also acts as a limit stop at this point when it engages the limit stop area 145 of housing 104, thereby also controlling electrode insertion depth.

Figure 22:
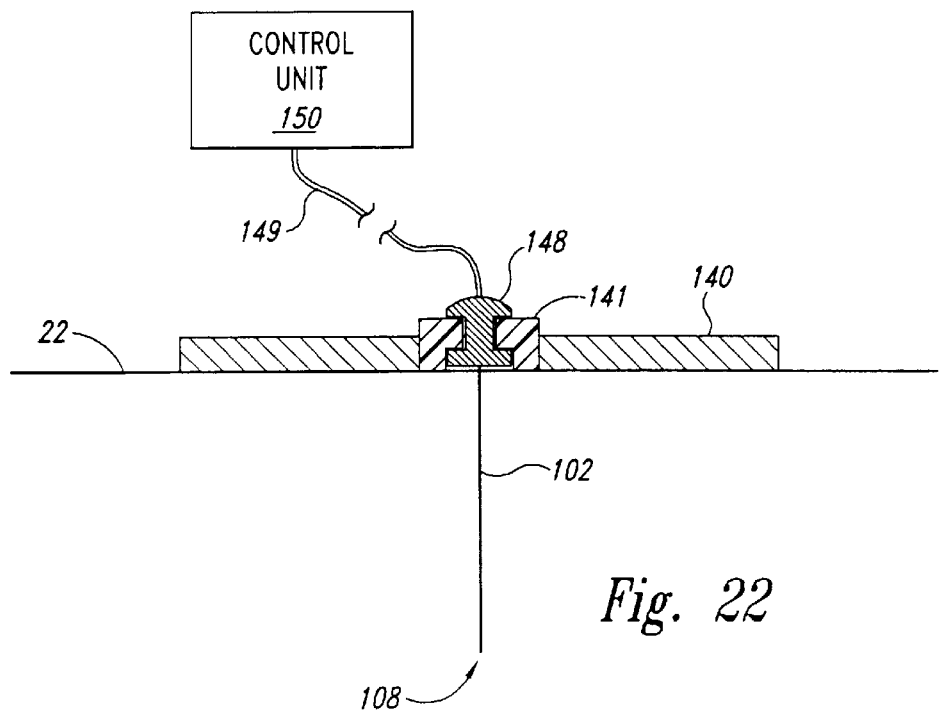
FIG. 22 is a sectional view of an inserted electrode assembly of the embodiment of FIGS. 13–16.
Figure 17:
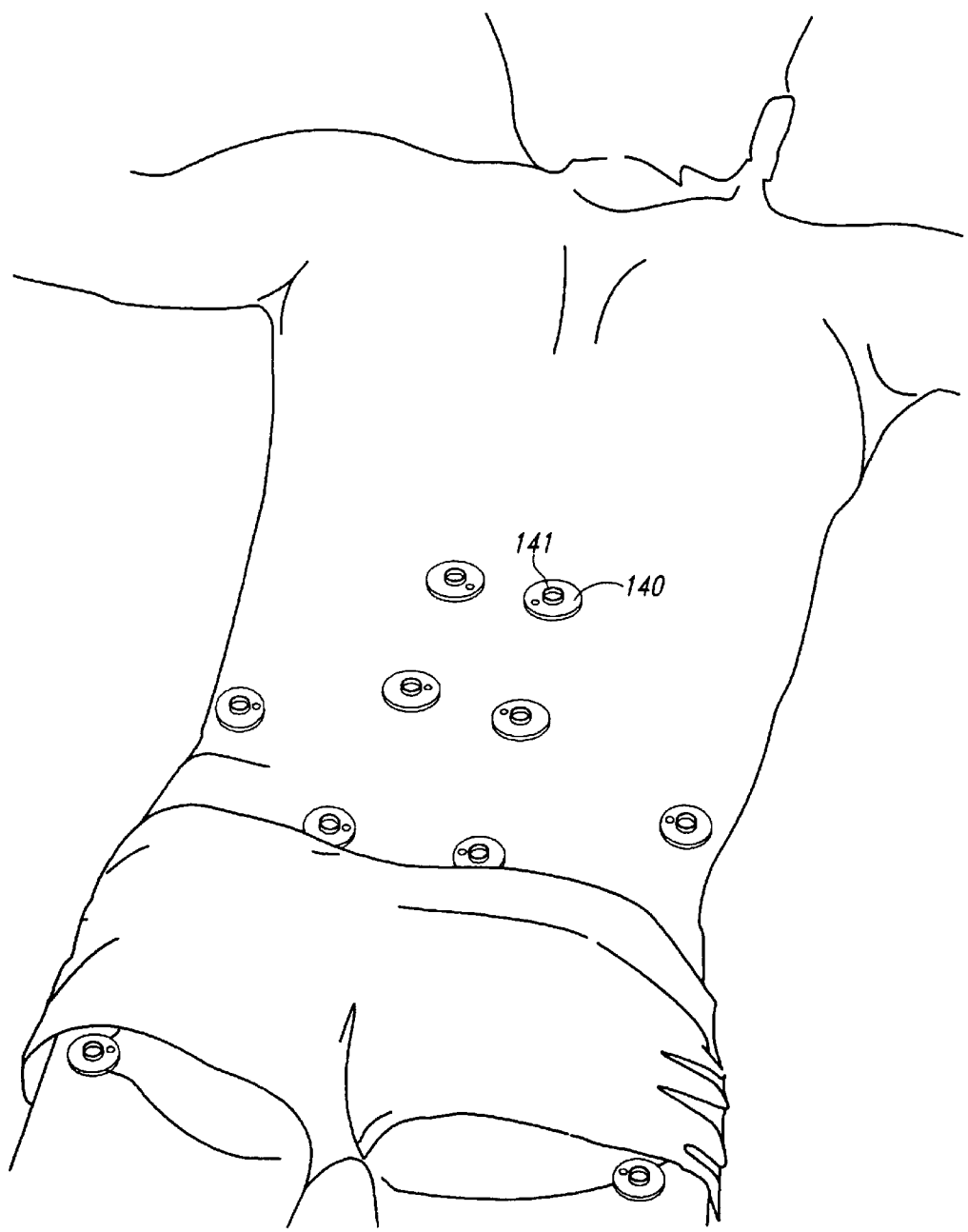
FIG. 17 shows part of the electrode assembly of the embodiment of FIGS. 13–16 in a montage used for treating low back pain using PNT.
Figure 21:
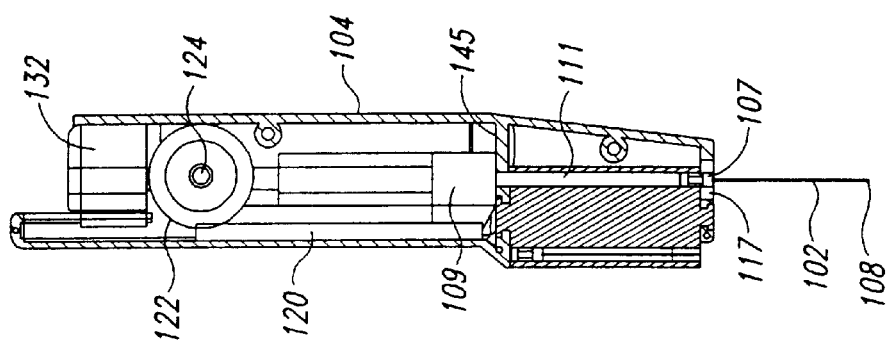
FIG. 21 is a sectional view showing the introducer of FIG. 13 in the process of deploying an electrode, also during insertion of the electrode.

Magazine 103 is rotated to a new insertion position and placed against an empty patch 140 after insertion of each electrode until all electrodes have been deployed and inserted. A suitable electrical connector 148 such as an alligator clip is electrically connected to electrode 102 through an aperture (not shown) formed in the upper larger diameter portion 112 of electrode handle 107 to provide electrical communication between a control unit 150 and electrode 102 via a cable or other conductor 149, as shown in FIG. 22. Patch 140 provides strain relief for electrode 102 by preventing tugging forces on cable 149 from dislodging the electrode from the patient, thereby helping keep the electrode in place.

Control unit 150 supplies stimulation current to the electrodes, e.g., in the manner described in the Ghoname et al. articles. Once again, the electrical waveform provided by the control unit depends on the application. For example, in an embodiment of a system providing percutaneous neuromodulation therapy, control unit 150 would preferably provide a current-regulated and current-balanced waveform with an amplitude of up to approximately 20 mA, frequency between approximately 4 Hz and 50 Hz, and pulse width of between approximately 50 $\mu$sec and 1 msec.

It should be noted that at no time during the electrode deployment, insertion and electrical therapy treatment processes was the sharp point of the electrode exposed to the operator or bystanders.

In an alternative embodiment, the lower wide portion of the electrode handle is formed from a rigid material and has rounded camming edges. The central annulus of patch 140 in this alternative embodiment is either compressible or has a resilient camming opening under the camming action of the electrode handle.

FIGS. 23–28 show a sharps-safe remover according to one embodiment of this invention. Remover 200 is designed to work with the electrode and electrode patch assembly described with respect to FIGS. 13–22 above. It should be understood that the principles of sharps-safe remover 200 may apply to other electrode designs as well.

Remover 200 has a housing 202 with an aperture 204 at its distal end. A number of previously undeployed electrodes 102 are stored within housing 202. A pair of rails 214 and 216 hold the electrodes 102 in alignment via the electrode handles 107, as shown. While this embodiment of the remover is designed to provide sharps-safe removal and storage of a plurality of electrodes, the invention applies to removers designed to remove and store one or any number of electrodes.

As described above, electrodes for percutaneous electrical therapy are inserted through a patient's skin into underlying tissue with handle portions exposed above the skin. The first step in undeploying and removing an inserted electrode is to line up the exposed handle 107 of an electrode with the remover's aperture 204, as shown in FIG. 23, by placing the distal face 205 of remover 200 against the patient's skin or against any portion of the electrode assembly (such as an adhesive patch) surrounding the electrode. While not shown in FIGS. 23–28, aperture 204 is sized to surround an annular member (such as annular member 141 discussed above) holding an electrode handle of an electrode assembly (such as that shown in FIGS. 13–22 above), the sharp point of which has been inserted through a patient's skin.

An electrode engagement fork 206 is pivotably attached to a longitudinally movable actuator 208 via an arm 209 and a hinged pivot 210. A coil spring 212 biases actuator 208 upwards towards the actuator and fork position shown in FIG. 28. A leaf spring 218 extends from arm 209. A cross-bar 220 at the end of leaf spring 218 slides in groove 222 and a corresponding groove (not shown) on the other side of housing 202. Leaf spring 218 is in its relaxed state in the position shown in FIG. 23. In this position, a cross-bar 224 extending from the distal end of arm 209 adjacent fork 206 lies at the top of a camming member 226 and a corresponding camming member (not shown) on the other side of housing 202.

Downward movement of actuator 208 (in response, e.g., to pressure from a user's thumb) against the upward force of spring 212 moves cross-bar 224 against a first camming surface 228 of camming member 226, as shown in FIG. 24. Camming surface 228 pushes cross-bar 224 of arm 209 against the action of leaf spring 218 as actuator 208, arm 209 and fork 206 move downward.

Figure 26:
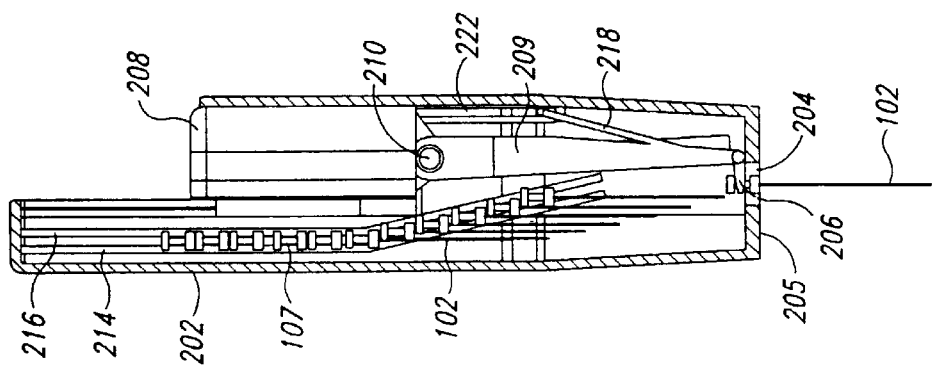
FIG. 26 is a partial sectional view of the electrode remover and angle of insertion assembly of FIG. 23 partially actuated and engaged with an electrode but prior to removal of the electrode.

FIG. 25 shows the limit of the downward movement of fork 206. At this point, cross-bar 224 clears the camming member 226, and leaf spring 218 rotates fork 206 and arm 209 about pivot 210 to engage fork 206 with electrode handle 107, as shown in FIG. 26. The tine spacing of fork 206 is shorter than the diameter of the upper wide portion 112 of electrode handle 107 but wider than the diameter of the narrow middle portion 113 of electrode handle 107.

Figure 27:
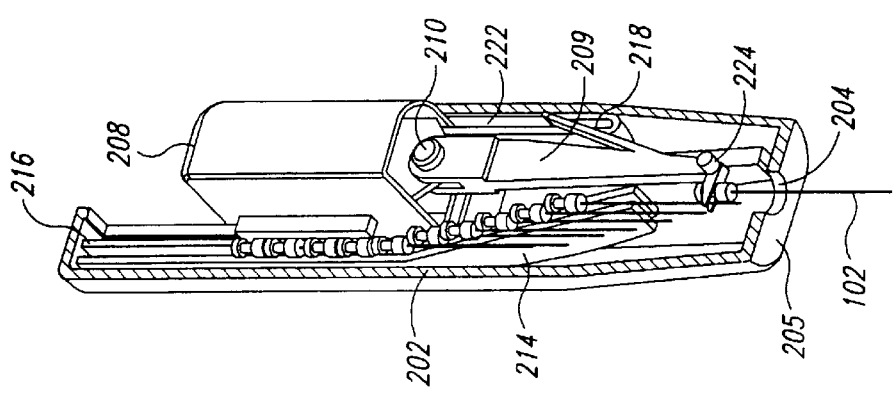
FIG. 27 is a partial sectional view of the electrode remover and angle of insertion assembly of FIG. 23 during removal of an electrode.

Release of actuator 208 by the user permits spring 212 to move actuator 208, arm 209 and fork 206 proximally. The engagement between fork 206 and electrode handle 107 causes the electrode to begin to move proximally with the fork out of the patient and into the remover housing, as shown in FIG. 27. At this point, cross-bar 224 is now engaged with a second camming surface 230 of camming member 226. Camming surface 230 pushes cross-bar 224 against the action of leaf spring 218 in the other direction (to the left in the view shown in FIG. 27) as the electrode, fork and arm rise under the action of coil spring 212.

Figure 28:
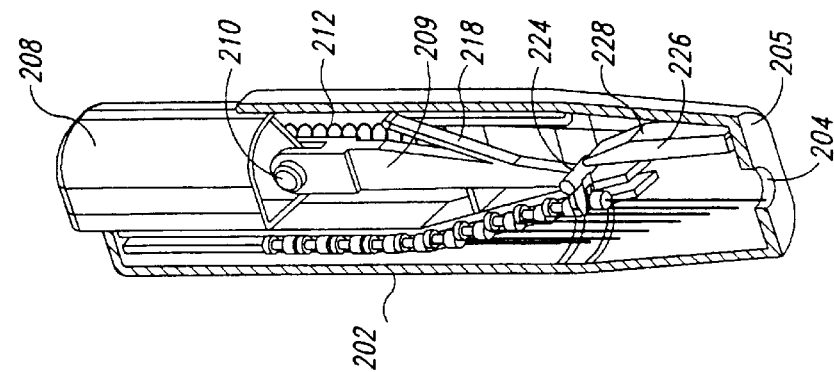
FIG. 28 is a partial sectional view of the electrode remover and angle of insertion assembly of FIG. 23 after removal of an electrode.

The electrode and fork continue to rise until they reach the upward limit of their permitted motion, as shown in FIG. 28. At this point, electrode handle 107 has engaged rails 214 and 216 and the most recent electrode previously stored in remover 200. Electrode handle 107 pushes against the electrode handle of the previously stored electrode handle, which in turn pushes against any electrode handles stored above it in the stack. In this manner, the latest electrode removed by remover 200 goes into the bottom of the stack of used electrodes stored in remover 200. Now that the sharp point 108 of electrode 102 is safely inside housing 202, remover 200 can be withdrawn from the site on the patient's skin through which the electrode had been inserted. Once cross-bar 224 clears the top of camming member 226, and leaf spring 218 moves arm 209 back to the center position shown in FIG. 23.

It should be noted that remover 200 provides sharp point protection for the entire electrode undeployment and removal process. Once all electrodes have been removed, the used electrodes can be safely transported in the sharps-safe container provided by the housing 202 of remover 200.

Modifications of the above embodiments of the invention will be apparent to those skilled in the art. For example, while the invention was described in the context of percutaneous electrical therapy in which electrodes are used to deliver electricity to a patient, the entry angle control features may be used with electrodes designed for medical monitoring and/or diagnosis. In addition, the entry angle control features of this invention may be used with acupuncture needles or other needles not used for conducting electricity to or from a patient.

What is claimed is:

1. A percutaneous electrical therapy system, comprising:
   a control unit configured to transmit an electrical therapy signal;
   an electrode electrically connectable to the control unit to deliver electrical therapy to a recipient, the electrode having a sharp point at a distal end configured to be inserted into tissue of the recipient;
   a housing having an actuator supporting the electrode and configured to control an angle of entry of the electrode into the tissue as the electrode moves relative to the housing, the housing having an aperture positioned to allow the electrode to pass through the housing into the tissue, the housing having an adhesive patch positioned to contact the tissue and releasably secure the housing to the tissue; and
   a mechanical connection between the electrode and the housing during insertion of the electrode into the patient's tissue, wherein the housing is adapted to be separated from the electrode after insertion of the electrode into the patient's tissue but before application of electrical therapy to the patient.

2. The system of claim 1 wherein the housing comprises a distal face adapted to be placed on the patient to control the angle between the housing and the patient.

3. The system of claim 2 wherein the housing further comprises an aperture in the distal face, the aperture being adapted to surround at least a portion of the electrode during insertion of the electrode into the patient's tissue.

4. The system of claim 2 wherein the distal face has a diameter greater than the housing's diameter.

5. The system of claim 1 wherein the electrode is adapted to move with respect to the housing during insertion of the electrode into the patient's tissue.

6. The system of claim 1 wherein the electrode and the housing are adapted to remain mechanically connected during application of electrical therapy to the patient.

7. The system of claim 1 wherein the electrode angle of insertion assembly further comprises a housing alignment member configured to be disposed on the patient's tissue and adapted to mechanically interact with the housing to align the housing with respect to the patient's tissue.

8. The system of claim 7 wherein the housing alignment member comprises a patch configured to be attached to the patient's tissue.

9. The system of claim 8 wherein the patch comprises an annular member adapted to mate with the housing and to surround the electrode during insertion of the electrode into the patient's tissue.

10. A method of performing percutaneous electrical therapy comprising:
    aligning an electrode assembly housing with a patient's tissue;
    releasably attaching the housing to the patient's tissue with an adhesive patch;
    inserting a sharp point of an electrode into the patient's tissue, the housing having an actuator supporting the electrode during insertion to control the electrode's angle of insertion; and
    applying an electrical signal to the electrode from a control unit; and
    removing the housing from the electrode after inserting the electrode and before applying the electrical signal to the electrode from the control unit.

11. A percutaneous electrical therapy system, comprising:
    a control unit configured to transmit an electrical therapy signal;
    an electrode electrically connectable to the control unit to deliver electrical therapy to a recipient, the electrode having a sharp point at a distal end configured to be inserted into tissue of the recipient; and
    a housing having an actuator supporting the electrode and configured to control an angle of entry of the electrode into the tissue as the electrode moves relative to the housing, the housing having an aperture positioned to allow the electrode to pass through the housing into the tissue, the housing having an adhesive patch positioned to contact the tissue and releasably secure the housing to the tissue, wherein the housing is separable from the electrode after the electrode is inserted into the tissue but before electrical therapy is administered to the patient.

12. A percutaneous electrical therapy system, comprising:

a control unit configured to transmit an electrical therapy signal;

an electrode electrically connectable to the control unit to deliver electrical therapy to a patient, the electrode comprising a sharp point at a distal end adapted to be inserted into the patient's tissue;

an electrode angle of insertion assembly configured to control the electrode's angle of entry into the patient's tissue, the electrode angle of insertion assembly comprising a housing supporting the electrode during insertion of the electrode into the patient's tissue, the housing being adapted to be separated from the electrode after insertion of the electrode into the patient's tissue but before application of electrical therapy to the patient, the electrode angle of insertion assembly further comprising a housing alignment member configured to be disposed on the patient's tissue and adapted to mechanically interact with the housing to align the housing with respect to the patient's tissue, the housing alignment member comprising a patch configured to be attached to the patient's tissue; and a mechanical connection between the electrode and the housing during insertion of the electrode into the patient's tissue.

13. The system of claim 12 wherein the patch comprises an annular member adapted to mate with the housing and to surround the electrode during insertion of the electrode into the patient's tissue.

* * * * *